US00RE42524E

(19) United States
(12) Reissued Patent
Tamarkin et al.

(10) Patent Number: US RE42,524 E
(45) Date of Reissued Patent: Jul. 5, 2011

(54) COLLOIDAL METAL COMPOSITIONS AND METHODS

(75) Inventors: Lawrence Tamarkin, Rockville, MD (US); Giulio F. Paciotti, Baltimore, MD (US)

(73) Assignee: Cytimmune Sciences, Inc., Rockville, MD (US)

(21) Appl. No.: 11/923,344

(22) Filed: Oct. 24, 2007

Related U.S. Patent Documents

Reissue of:
(64) Patent No.: 7,229,841
Issued: Jun. 12, 2007
Appl. No.: 10/093,578
Filed: Mar. 8, 2002

U.S. Applications:
(60) Provisional application No. 60/287,363, filed on Apr. 30, 2001.

(51) Int. Cl.
*G01N 33/553* (2006.01)
(52) U.S. Cl. ..... 436/525; 436/518
(58) Field of Classification Search ..... 435/518, 435/525; 436/518, 525; 424/193.1, 85, 85.1, 424/617; 514/2, 12; 530/350
See application file for complete search history.

(56) References Cited

U.S. PATENT DOCUMENTS

| | | | |
|---|---|---|---|
| 2,768,958 | A | 10/1956 | Stewart et al. |
| 2,785,153 | A | 3/1957 | Locke et al. |
| 3,145,144 | A | 8/1964 | Ando et al. |
| 3,149,036 | A | 9/1964 | Woodhour et al. |
| 3,269,912 | A | 8/1966 | Grafe |
| 3,399,263 | A | 8/1968 | Strazdins et al. |
| 3,531,565 | A | 9/1970 | Webb et al. |
| 3,577,523 | A | 5/1971 | Stolar et al. |
| 3,651,211 | A | 3/1972 | Gillchriest et al. |
| 3,819,820 | A | 6/1974 | Lorina et al. |
| 3,919,413 | A | 11/1975 | Mebus |
| 3,983,228 | A | 9/1976 | Woodhour et al. |
| 4,016,252 | A | 4/1977 | Relyveld |
| 4,053,587 | A | 10/1977 | Davidson et al. |
| 4,069,313 | A | 1/1978 | Woodhour et al. |
| 4,177,263 | A | 12/1979 | Rosenberg et al. |
| 4,196,185 | A | 4/1980 | Focella et al. |
| 4,197,237 | A | 4/1980 | Leute et al. |
| 4,197,286 | A | 4/1980 | Rao |
| 4,213,964 | A | 7/1980 | Buckler |
| 4,215,036 | A | 7/1980 | Malley |
| 4,218,436 | A | 8/1980 | Fitzpatrick |
| 4,329,281 | A | 5/1982 | Christenson et al. |
| 4,330,530 | A | 5/1982 | Baker |
| 4,332,787 | A | 6/1982 | Homcy et al. |
| 4,339,437 | A | 7/1982 | Rosenberg et al. |
| 4,346,074 | A | 8/1982 | Gilmour et al. |
| 4,451,570 | A | 5/1984 | Royston et al. |
| 4,487,780 | A | 12/1984 | Scheinberg |
| 4,578,270 | A | 3/1986 | Csizer et al. |
| 4,594,325 | A | 6/1986 | Lundak |
| 4,608,252 | A | 8/1986 | Khanna et al. |
| 4,624,921 | A | 11/1986 | Larrick et al. |
| 4,624,923 | A | 11/1986 | Margel |
| 4,639,336 | A | 1/1987 | Jouquey et al. |
| 4,657,763 | A | 4/1987 | Finkelstein |
| 4,693,975 | A | 9/1987 | Kozbor et al. |
| 4,710,378 | A | 12/1987 | Ohtomo et al. |
| 4,720,459 | A | 1/1988 | Winkelhake |
| 4,740,589 | A | 4/1988 | Moreno |
| 4,744,760 | A | 5/1988 | Molday |
| 4,753,873 | A | 6/1988 | Beltz et al. |
| 4,812,556 | A | 3/1989 | Vahlne et al. |
| 4,880,750 | A | 11/1989 | Francoeur |
| 4,882,423 | A | 11/1989 | Taguchi et al. |
| 4,906,564 | A | 3/1990 | Lyon et al. |
| 4,977,286 | A | 12/1990 | Nicolaou et al. |
| 5,017,687 | A | 5/1991 | Vahlne et al. |
| 5,019,497 | A | 5/1991 | Olsson |
| 5,035,995 | A | 7/1991 | Taguchi et al. |
| 5,089,424 | A | 2/1992 | Khalil et al. |
| 5,112,606 | A | 5/1992 | Shiosaka et al. |
| 5,126,253 | A | 6/1992 | Nakanishi et al. |
| 5,169,754 | A | 12/1992 | Siiman et al. |
| 5,213,804 | A | 5/1993 | Martin et al. |
| 5,242,828 | A | 9/1993 | Bergstrom et al. |
| 5,248,772 | A | 9/1993 | Siiman et al. |
| 5,264,221 | A | 11/1993 | Tagawa et al. |
| 5,294,369 | A | 3/1994 | Shigekawa et al. |
| 5,376,556 | A | 12/1994 | Tarcha et al. |
| 5,384,073 | A | 1/1995 | Shigekawa et al. |
| 5,434,088 | A | 7/1995 | Ikeda et al. |

(Continued)

FOREIGN PATENT DOCUMENTS

| | | |
|---|---|---|
| AU | 760035 | 8/2003 |

(Continued)

OTHER PUBLICATIONS

Office Action in U.S. Appl. No. 11/046,204, filed Oct. 16, 2008.

Author: Ciesiolka et al., Title: An 8- to 10-fold Enhancement in Sensitivity for Quanitation of Proteins by Modified Application of Colloidal Gold (Abstract Only—Applicants do not have complete copy), Publ: *Analytical Biochemistry,* vol./Iss: 168 (2), pp. 280-283, Date: Feb. 1, 1988.

Author: Debrabander et al., Title: Probing Microtobule-Dependent Intracellular Motility with Nanometre Particle Video Ultramicroscopy (nanovid ultramicroscopy) (Abstract Only—Applicants do not have complete copy), Publ: *Cytobio,* vol./Iss: 43, pp. 273-283, Date: Jan. 1, 1985.

Author: Deng et al., Title: Self-Assembled Monolayers of Alkanethiolates Presenting Tri(propylene sulfoxide) Groups Resist the Adsorption of Protein, Publ: *Journal of the American Chemical Society,* vol./Iss: 118(19), pp. 5136-5137, Date: May 15, 1996.

(Continued)

*Primary Examiner* — J. E Angell
(74) *Attorney, Agent, or Firm* — Johnson & Associates

(57) ABSTRACT

The present invention comprises compositions and methods for delivery systems of agents, including therapeutic compounds, pharmaceutical agents, drugs, detection agents, nucleic acid sequences and biological factors. In general, these vector compositions comprise a colloidal metal, derivatized PEG (polyethylene glycol) and an agent. The invention also comprises methods and compositions for making such colloidal metal compositions and for treatment of cancer.

5 Claims, 14 Drawing Sheets

U.S. PATENT DOCUMENTS

| | | | | |
|---|---|---|---|---|
| 5,436,161 | A | 7/1995 | Bergstrom et al. | |
| 5,446,090 | A | 8/1995 | Harris | |
| 5,466,609 | A | 11/1995 | Siiman et al. | |
| 5,498,421 | A | 3/1996 | Grinstaff et al. | |
| 5,521,289 | A | 5/1996 | Hainfeld et al. | |
| 5,639,725 | A | 6/1997 | O'Reilly et al. | |
| 5,686,578 | A | 11/1997 | Goldenberg | |
| 5,736,410 | A | 4/1998 | Zarling et al. | |
| 5,874,226 | A | 2/1999 | Zeytinoglu et al. | |
| 5,921,927 | A | 7/1999 | McArdle | |
| 5,972,720 | A | 10/1999 | Nichtl et al. | |
| 6,235,093 | B1 | 5/2001 | Okuhama et al. | |
| 6,274,552 | B1 * | 8/2001 | Tamarkin et al. | 514/12 |
| 6,407,218 | B1 | 6/2002 | Tamarkin et al. | |
| 6,447,765 | B1 | 9/2002 | Horwitz | |
| 6,528,051 | B2 | 3/2003 | Tamarkin et al. | |
| 6,528,485 | B1 * | 3/2003 | Veronese et al. | 514/12 |
| 6,530,944 | B2 | 3/2003 | West et al. | |
| 6,541,617 | B1 | 4/2003 | Bamdad et al. | |
| 6,624,886 | B2 | 9/2003 | Natan et al. | |
| 6,660,058 | B1 | 12/2003 | Oh et al. | |
| 6,869,932 | B2 | 3/2005 | Veronese et al. | |
| 7,229,841 | B2 | 6/2007 | Tamarkin et al. | |
| 2001/0055581 | A1 | 12/2001 | Tamarkin et al. | |
| 2002/0103517 | A1 | 8/2002 | West et al. | |
| 2002/0192814 | A1 | 12/2002 | Tamarkin et al. | |
| 2003/0053983 | A1 | 3/2003 | Tamarkin et al. | |
| 2003/0180252 | A1 | 9/2003 | Tamarkin et al. | |
| 2004/0018203 | A1 * | 1/2004 | Pastan et al. | 424/178.1 |
| 2004/0029794 | A1 | 2/2004 | Veronese et al. | |
| 2004/0180002 | A1 | 9/2004 | Young et al. | |
| 2004/0213760 | A1 | 10/2004 | Tamarkin et al. | |
| 2005/0003431 | A1 | 1/2005 | Wucherpfennig et al. | |

FOREIGN PATENT DOCUMENTS

| | | | |
|---|---|---|---|
| AU | 757857 | | 3/2004 |
| AU | 2003204353 | | 11/2006 |
| CA | 2158475 | | 3/1994 |
| EP | 0 044 722 | | 1/1982 |
| EP | 0 044 722 | A1 | 1/1982 |
| EP | 0 156 242 | | 12/1985 |
| EP | 0 179 483 | | 4/1986 |
| EP | 0 179 483 | B1 | 4/1986 |
| EP | 0 269 408 | A3 | 11/1987 |
| EP | 0 269 408 | | 6/1988 |
| EP | 0 486 526 | B1 | 2/1991 |
| EP | 0 441 120 | A2 | 8/1991 |
| EP | 0 489 465 | A2 | 6/1992 |
| EP | 0 667 398 | A2 | 8/1995 |
| EP | 0 811 846 | B1 | 12/1997 |
| EP | 0 486 526 | B2 | 3/2001 |
| EP | 1 342 518 | A1 | 9/2003 |
| EP | 1 401 376 | | 3/2004 |
| EP | 0 690 722 | B1 | 6/2004 |
| EP | 1 039 933 | B1 | 2/2006 |
| EP | 1 044 022 | B1 | 3/2006 |
| FR | 2 533 827 | | 4/1984 |
| GB | 981242 | | 1/1965 |
| JP | 05-017369 | | 1/1993 |
| JP | 6-118083 | | 4/1994 |
| JP | 11-124335 | | 5/1999 |
| JP | 2000-100210 | | 6/2000 |
| WO | WO 90/05303 | A1 | 5/1990 |
| WO | WO 91/02078 | A1 | 2/1991 |
| WO | WO 91/15242 | A1 | 10/1991 |
| WO | WO 93/15117 | | 8/1993 |
| WO | WO 93/21528 | A1 | 10/1993 |
| WO | WO 94/18954 | A1 | 9/1994 |
| WO | WO 94/21240 | A2 | 9/1994 |
| WO | WO 94/21288 | | 9/1994 |
| WO | WO 94/21288 | A1 | 9/1994 |
| WO | WO 95/24918 | A1 | 9/1995 |
| WO | WO 96/04313 | | 2/1996 |
| WO | WO 97/29131 | A1 | 8/1997 |
| WO | WO 99/24066 | | 5/1999 |
| WO | WO 9924077 | A2 * | 5/1999 |
| WO | WO 01/95942 | A2 | 12/2001 |
| WO | WO 2002/087509 | A2 | 11/2002 |
| WO | WO 2005/072893 | A1 | 8/2005 |

OTHER PUBLICATIONS

Author: Elliott et al., Title: Analysis of Colloidal Gold Probes by Isoelectric Focusing in Agarose Gels (Abstract Only—Applicants do not have complete copy), Publ: *Analytical Biochemisty,* vol./Iss: 186(1), pp. 53-59, Date: Apr. 1, 1990.

Author: Grainger et al., Title: Polymeric Monolayers on Solid Substrates by Spontaneous Adsorption from Solution, Publ: *American Chemical Society—Abstracts of Papers,* vol./Iss: Part 1, Pages: Paragraph 074, Date: Aug. 20, 1995.

Author: Lang et al., Title: A New Class of Thiolipids for the Attachment of Lipid Bilayers on Gold Surfaces, Publ: *Langmuit,* vol./Iss: 10(1), pp. 197-210, Date: Jan. 1, 1994.

Author: Lemmon et al., Title: Preparation and Characterization of Nanocomposites of Poly(ethylene oxide) with Layered Solids, Publ:, vol./Iss:, pp. 43-54, Date: Jan. 1, 1995.

Author: Leuvering et al., Title: A Sol Particle Agglutination Assay for Human Chorionic Gonadotrophin (Abstract Only—Applicants do not have complete copy), Publ: *Journal of Immunological Methods,* vol./Iss: 45(2), pp. 183-194, Date: Jan. 1, 1981.

Author: Lezzi et al., Title: Chelating Resins Supporting Dithiocarbamate and Methylthiourea Groups in Adsorption of Heavy Metal Ions, Publ: *Journal of Applied Polymer Science,* vol./Iss: 54(7), pp. 889-897, Date: Nov. 14, 1994.

Author: Lezzi et al., Title: Synthesis of Thiol Chelating Resins and Their Adsorption Properties toward Heavy Metal Ions, Publ: *Journal of Polymer Science,* vol./Iss: 32, pp. 1877-1883, Date: Jan. 1, 1994.

Author: Li et al., Title: Plasma Protein Interactions with Copolymer-Stabilized Colloids, Publ: *Dissertation Abstracts International,* vol./Iss: 54(7), pp. 3735-B, Date: Jan. 1, 1994.

Author: Mathias et al., Title: Sulfur-Substituted Polyoxyethylenes Sequential Ether-Thioether Copolymers, Publ: *Crown Ethers and Phase Transfer Catalysis in Polymer Science,* vol./Iss:, pp. 359-370, Date: Jan. 1, 1984.

Author: Mrksich et al., Title: Surface Plasmon Resonance Permits in Situ Measurement of Protein Adsorption on Self-Assembled Monolayers of Alkanethiolates on Gold, Publ: *Langmuir,* vol./Iss: 11, pp. 4383-4385, Date: Jan. 1, 1995.

Author: Nakashima et al., Title: Electrochemical Characterization of an Assembled Monolayers of α-Methoxy-ωmercapto-poly(ethylene glycol) on Gold and Complex Formation of the Monolayer with α-Cyclodextrin, Publ: *Chemistry Letters,* vol./Iss:, pp. 731-732, Date: Jan. 1, 1996.

Author: Niwa et al., Title: Two-Dimensional Array of Poly(methacrylic acid) Brushes on Gold Substrates. Interaction with Ferrocen-Terminated Poly(oxyethylene)s, Publ: *Macromolecules,* vol./Iss: 28(23), pp. 7770-7774, Date: Nov. 6, 1995.

Author: Prime et al., Title: Adsorption of Proteins onto Surfaces Containing End-Attached Oligo(ethylene oxide): A Model System Using Self-Assembled Monolayers, Publ: *Journal of the American Chemical Society,* vol./Iss: 115, pp. 10714-10721, Date: Jan. 1, 1993.

Author: Rabolt, J.F., Title: Design and Construction of Two Component Heterogenous Polymer Surfaces by Self Assembly, Publ: *Polymer Preprints*, vol./Iss: 36(1), pp. 84, Date: Apr. 1, 1995.

Author: Vidal et al., Title: Steric Stabilization of Polystyrene Colloids Using Thiol-ended Polyethylene Oxide, Publ: *Polymers for Advanced Technologies,* vol./Iss: 6, pp. 473-479, Date: Nov. 15, 1994.

Author:, Title: "Cancer", Publ: *Taber's Cyclopedic Medical Disctionary,* vol./Iss: Ed. 16, pp. 274, Date: Jan. 1, 1985.

Author: Balkwill et al., Title: The Cytokine Network, Publ: *Immunology Today,* vol./Iss: 10(9), pp. 299-304, Date: Jan. 1, 1989.

Author: Brust et al., Title: Novel Gold-Dithiol Nano-Networks with Non-Metalhe Electronic Properties, Publ: *Advanced Materials,* vol./Iss: 7(9), pp. 795-797, Date: Jan. 1, 1995.

Author: Carter et al., Title: Appendix C, Publ: *Chemotherapy of Cancer,* vol./Iss: 2nd Ed., pp. 361-367, Date: Jan. 1, 1981.

Author: Cohen, I., Title: Optimization of Dose-Time Factors for a Tumor and Multiple Associated Normal Tissues, Publ: *International Journal of Radiation Oncology,* vol./Iss: 13, pp. 251-258, Date: Jan. 1, 1987.
Author: Coulombe et al., Title: Cytochemical Demonstrations of Increased Phospholipid Content in Cell Membranes in Chlorphentermine-Induced Phospholipidosis, Publ: *Journal of Histochemistry and Cytochemistry,* vol./Iss: 37(2), pp. 139-147, Date: Jan. 1, 1989.
Author: Eck et al., Title: Chapter 5: Gene-Based Therapy, Publ: *Goodman & Gilman's The Pharmacological Basis of Therapeutics,* vol./Iss:, pp. 77-101, Date: Jan. 1, 1996.
Author: EPO Searching Authority, Title: Search Report EPO—Application No. 02729092.3, Publ: *EPO Search Report,* vol./Iss:, pp. 1-6, Date: Jul. 13, 2009.
Author: Fraker et al., Title: Passive Immunization Against Tumor Necrosis Factor Partially Abrogates Interleukin 2 Toxicity, Publ: *The Journal of Experimental Medicine,* vol./Iss: 170, pp. 1015-1020, Date: Jan. 1, 1989.
Author: Goldstein et al., Title: Cardiovascular Effects of Platelet-Activating Factor, Publ: *Lipids,* vol./Iss: 26(212), pp. 1250-1256, Date: Jan. 1, 1991.
Author: Gref et al., Title: The Controlled Intravenous Delivery of Drugs using PEG-Coated Sterically Stabilized Nanospheres, Publ: *Advanced Drug Delivery Reviews,* vol./Iss: 16, pp. 215-233, Date: Jan. 1, 1995.
Author: Gura, T., Title: Systems for Identifying New Drug are Often Faulty, Publ: *Science,* vol./Iss: 278, pp. 1041-1042, Date: Nov. 7, 1997.
Author: Hashimoto et al., Title: Action Site of Circulating Interleukin-1 on the Rabbit Brain, Publ: *Brain Research,* vol./Iss: 540, pp. 217-223, Date: Jan. 1, 1991.
Author: Hisamatsu et al., Title: Platelet Activating Factor Induced Respiratory Mucosal Damage, Publ: *Lipds,* vol./Iss: 26(12), pp. 1287-1291, Date: Jan. 1, 1991.
Author: Hopkins et al., Title: Early Events Following the Binding of Epidermal Growth Factor to Surface Receptors on Ovarian Granulosa Cells, Publ: *European Journal of Cell Biology,* vol./Iss: 24, pp. 259-264, Date: Jan. 1, 1981.
Author: Kang et al., Title: Ultrastructural and Immunocytochemical Study of the Uptake and Distribution of Bacterial Lipopolysaccharide in Human Monocytes, Publ: *Journal of Leukemia Biology,* vol./Iss: 48, pp. 316-332, Date: Jan. 1, 1990.
Author: Kirchner et al., Title: The Development of Neutralizing Antibodies in a Patient Receiving Subcutaneous Recombinant and Natural Interleukin-2, Publ: *Cancer,* vol./Iss: 67(7), pp. 1862-1864, Date: Apr. 1, 1991.
Author: Koning, et al., Title: Selective Transfer of a Lipophilic Prodrug of 5-Fluorodeoxyuridine from Immunoliposomes to Colon Cancer Cells, Publ: *Biochimica et Biphysica Acta,* vol./Iss: 1420, pp. 153-167, Date: Jun. 2, 1999.
Author: Krontiris, T.G., Title: Chapter 71: Molecular and Cellular Biology of Cancer, Publ: *Internal Medicine,* vol./Iss: 4th Ed., pp. 699-729, Date: Jan. 1, 1994.
Author: Lanzavecchia, Title: Identifying Strategies for Immune Interveator, Publ: *Science,* vol./Iss: 260, pp. 937-944, Date: Jan. 1, 1993.
Author: Marshall, E., Title: Gene Therapy's Growing Pains, Publ: *Science,* vol./Iss: 269(5227), pp. 1050-1055, Date: Aug. 25, 1995.
Author: Maruyama et al., Title: Targeting Efficiency of PEG-Immunoliposome-Conjugated Antibodies at PEG Terminals (Abstract Only-Applicants do not have comple copy), Publ: *Advanced Drug Delivery Reviews,* vol./Iss: 24, pp. 235-242, Date: Mar. 17, 1997.
Author: Morris et al., Title: Validation of the Biotinyl Ligant-Avidin-Gold Technique, Publ: *Cyctochemistry,* vol./Iss: 40, pp. 711-721, Date: Jan. 1, 1992.
Author: Ormann et al., Title: Expression of Tumor Necrosis Factor-α Receptors on Bovine Macrophages, Lymphocytes and Polymorphonuclear Luekocytes Internalization of Receptor-Bound Ligand, and Some Functional Effects, Publ: *Lymphokine Research,* vol./Iss: 9(1), pp. 43-58, Date: Jan. 1, 1990.
Author: Otsuka et el., Title: Quantitative and Reversible Lectin-Induced Association of Gold Nanoparticles Modified with α-Lactosyl-ω-mercapto-poly(ethylene glycol), Publ: *Journal of the American Chemical Society,* vol./Iss: 123, pp. 8226-8230, Date: Feb. 20, 2001..
Author: Paciotti et al., Title: Interleukin 2 Differentially Effects the Proliferation of a Hormone-Dependent and a Hormone-Independent Human Breast Cancer Cell Line in Vitro and in Vivo, Publ: *Anti-Cancer Research,* vol./Iss: 8, pp. 1233-1249, Date: Jan. 1, 1988.
Author: Paciotti et al., Title: Interleukin 1α Differentially Synchronizes Estrogen Dependent and Estrogen-Independent Human Breast Cells in $G_0/G_1$ Phase of the Cell Cycle, Publ: *Anti-Cancer Research,* vol./Iss: 11, pp. 25-32, Date: Jan. 1, 1991.
Author: Paciotti et al., Title: Interleukin 1 Directly Regulates Hormone-Dependent Human Breast Cancer Cell Proliferation in Vivo, Publ: *Molecular Endocrinology,* vol./Iss: 2, pp. 459-464, Date: Jan. 1, 1988.
Author: Paciotti et al., Title: (XP-001537146) #3858—Comparison of the Toxicity and Pharmacokinetics of Neat and Colloidal Gold Bound TNF, Publ: *Proceedings of the American Association for Cancer Research,* vol./Iss: 40, pp. 585, Date: Mar. 1, 1999.
Author: Paciotti et al., Title: (XP-001537149) #1048—The Use of Colloidal Gold in Cytokine Immunotherapy, Publ: *Proceedings of the American Association for Cancer Research,* vol./Iss: 39, pp. 153, Date: Mar. 1, 1998.
Author: Peters et al., Title: Binding and Internalization of Biotinylated Interleukin-2 in Human Lymphocytes, Publ: *Blood,* vol./Iss: 76, pp. 97-104, Date: Jan. 1, 1990.
Author: Prakken et al., Title: Artificial Antigen-Presenting Cells as a Tool to Exploit the Immune 'Synapse', Publ: *Nature Medicine,* vol./Iss: 6(12), pp. 1406-1410, Date: Dec. 1, 2000.
Author: Roitt et al., Title: The Cytokine Network, Publ: *Immunology,* vol./Iss: 3rd Ed., pp. 8-15, Date: Jan. 1, 1993.
Author: Ross et al., Title: Gene Therapy in the United States: A Five-Year Status Report, Publ: *Human Gene Therapy,* vol./Iss: 7, pp. 1781-1790, Date: Sep. 10, 1996.
Author: Rubanyi, G.M., Title: The Future of Human Gene Therapy, Publ: *Molecular Aspects of Medicine,* vol./Iss: 22, pp. 113-142, Date: Jan. 1, 2001.
Author: Schmitmeier et al., Title: Anti-Invasive Effect of Contortrostatin. A snake Venom Disintegrin, and TNF-alpha on Malignant Glioma Cells-(Applicants do not have complete copy), Publ: *Anti-Cancer Research,* vol./Iss: 20(6B), pp. 4227-4233, Date: Nov. 1, 2000.
Author: Tannock et al., Title:, Publ: *The Basic Science of Oncology,* vol./Iss: 2nd Ed., pp. 352-353, Date: Jan. 1, 1992.
Author: Tomii et al., Title: Production of Anti-Platelet-Activating Factor Antibodies by the Use of Colloidal Gold as Cancer, Publ: *Japane Journal of Medicinal Science and Biology,* vol./Iss: 44, pp. 75-80, Date: Jan. 1, 1991.
Author: USPTO, Title: USPTO Office Action—cited in 11/805,383, Publ: *USPTO Office Action,* vol./Iss:, pp. 1-16, Date: Apr. 17, 2009.
Author: USPTO, Title: USPTO Office Action—cited in 11/805,383, Publ: *USPTO Office Action,* vol./Iss:, pp. 1-33, Date: Aug. 19, 2009.
Author: Van Rensen et al., Title: Liposomes with Incorporated MHC Class II/Peptide Complexes as Antigen Presenting Vesicles for Specific T Cell Activation, Publ: *Pharmaceutical Research,* vol./Iss: 16(2), pp. 198-204, Date: Jan. 1, 1999.
Author: Verma et al., Title: Gene Therapy—Promises, Problems and Prospects, Publ: *Nature,* vol./Iss: 389, pp. 239-242, Date: Sep. 18, 1997.
Author: Walden et al., Title: Induction of Regulatory T-lymphocyte Responses by Liposomes Carrying Major Histocompatibility Complex Molecules and Foreing Antigen, Publ: *Nature,* vol./Iss: 315, pp. 327-329, Date: May 23, 1985.
Author: Wuelling et al., Title: Nanometer Gold Clusters Protected by Surface-Bound Monolayers of Thiolated Poly (ethylene glycol) Polymer Electrolyte, Publ: *Journal of the American Chemical Society,* vol./Iss: 120, pp. 12696-12697, Date: Jan. 1, 1998.
Author:, Title: Japanese Office Action cited in 2006-551620 (with English translation), Publ: *Japanese Office Action,* vol./Iss:, pp. 1-4, Date: Jul. 13, 2010.
Author:, Title: Canadian Office Action—Application No. 2,448,607, Publ: *Canadian Office Action,* vol./Iss:, pp. 1-4, Date: Apr. 7, 2009.

Author:, Title: Australian Office Action—Application No. 2002259107, Publ: *Australian Office Action,* vol./Iss:, pp. 1-2, Date: Nov. 14, 2005.
Author:, Title: Appicants do not have translation; Concise Statement: This reference describes the use of acetal-PEG-dimethylaminotheylpolymethacrylate as a dispersion stabilizer for fine particles of gold, Publ: *Polymer Preprints,* vol./Iss: 49(3), pp. 650, Date: Jan. 1, 2000.
Author:, Title: Japanese Office Action cited in 2002-584861 (with English translation), Publ: *Japanese Office Action,* vol./Iss:, pp. 1-10, Date: Dec. 25, 2008.
Author: IBM TDB et al., Title: Molecular Glue for Highly Controlled Attachment of Macromolecules to Metals, Publ: *IBM Technical Bulletin,* vol./Iss: 39(09), pp. 1-5, Date: Sep. 1, 1996.
Author: Klotz et a., Title: Macromolecule-Small Molecule Interactions: Strong Binding by Intramolecularly Cross-Linked Polylysine, Publ: *Biochemistry,* vol./Iss: 10(6), pp. 923-926, Date: Jan. 1, 1971.
Author: Magez et al., Title: Specific Uptake Tumor Necrosis Factor—a is Involved in Growth Control of *Trypanosoma brucei,* Publ: *The Journal of Cell Biology,* vol./Iss: 137(3), pp. 715-727, Date: May 5, 1997.
Author: USPTO, Title: USPTO Office Action—cited in 11/516,175, Publ: *USPTO Office Action,* vol./Iss:, pp. 1-10, Date: Sep. 11, 2009.
Author: Wink et al., Title: Interation Between Plasmid DNA and Cationic Polymers Studied by Surface Plasmon Resonance Spectrometry Publ: *Analytical Chemistry,* vol./Iss: 71, pp. 801-805, Date: Jan. 1, 1999.
Author: Illum et al., Title: Development of Systems for Targeting the Regional Lymph Nodes for Diagnostic Imaging: In Vivo Behavior of Colloidal PEG-Coated Magnetic Nanospheres in the Rat Following Intestinal Administration, Publ: *Pharmaceutical Research,* vol./Iss: 18(5), pp. 640-645, Date: Jan. 1, 2001.
Author: USPTO, Title: USPTO Office Action—cited 11/516,175, Publ: *USPTO Office Action,* vol./Iss:, pp. 1-9, Date: Jun. 5, 2009.
Author:, Title: Japanese Office Action cited in 2000-520162 (with English translation), Publ: *Japanese Office Action,* vol./Iss:, pp. 1-3, Date: Jun. 4, 2010.
Author:, Title: Japanese Office Action cited in 2000-520162 (with English translation), Publ: *Japanese Office Action,* vol./Iss:, pp. 1-3, Date: Oct. 22, 2009.
Author:, Title: Japanese Office Action cited in 2000-520162 (with English translation), Publ: *Japanese Office Action,* vol./Iss:, pp. 1-7, Date: Apr. 14, 2009.
Author:, Title: EPO Search Report—98957757.2, Publ: *EPO Search Report,* vol./Iss:, pp. 1-4, Date: Oct. 31, 2003.
Author:, Title: EPO Search Report—98957757.2, Publ: *EPO Search Report,* vol./Iss:, pp. 1-3, Date: Oct. 31, 2003.
Author:, Title: Canadian Office Action—2,309,604, Publ: *Canadian Office Action,* vol./Iss:, pp. 1-4, Date: Feb. 11, 2006.
Author:, Title: Canadian Office Action—2,309,604, Publ: *Canadian Office Action,* vol./Iss:, pp. 1-4, Date: May 18, 2006.
Author:, Title: EPO Search Report cited in EP Application No. 05722719.9 (CYT-0094EP) Publ: *EPO Search Report,* vol./Iss:, pp. 1-4, Date: Sep. 15, 2010.
Author:, Title: PCT International Search Report and Written Opinion issued in PCT/US08/77239 (CYT-0166) Publ: *PCT International Search Report,* vol./Iss:, pp. 107, Date: Dec. 5, 2008.
Author:, Title: Office Action—Peoples Republic of China—Application No. 200580009719.0 (with English translation) Publ: *Peoples Republic of China—Office Action,* vol./Iss:, pp. 1-15, Date: Mar. 20, 2009.
Author:, Title: USPTO Office Action—cited in 10/672,144, Publ: *USPTO Office Action,* vol./Iss:, pp. 1-10, Date: Apr. 15, 2009.
Author:, Title: USPTO Office Action—cited in 10/672,144, Publ: *USPTO Office Action,* vol./Iss:, pp. 1-8, Date: Jan. 20, 2010.
Author:, Title: USPTO Office Action—cited in 10/672,144 (CYT-0027), Publ: *USPTO Office Action,* vol./Iss:, pp. 1-5, Date: Nov. 15, 2010.
Author:, Title: USPTO Office Action—cited in 10/672,144, Publ: *USPTO Office Action,* vol./Iss:, pp. 1-8, Date: Oct. 17, 2007.
Author:, Title: USPTO Office Action—cited in 10/672,144, Publ: *USPTO Office Action,* vol./Iss:, pp. 1-6, Date: Aug. 5, 2010.
Author: Calabrese et al., Title: Chemotherapy of Neoplastic Diseases, Publ: *Goodman & Gilman's The Pharmacological Basis of Therapeutics,* vol./Iss: 9th Edition, pp. 1260-1261, Date: Jan. 1, 1996.
Author: De Roe et al., Title: A Model of Protein—Colloidal Gold Interactions, Publ: *The Journal of Histochemistry and Cytochemistry,* vol./Iss: 35(11), pp. 1191-1198, Date: Jan. 1, 1987.
Author: Dominguez et al., Title: Effect of Heat Treatment on the Antigen-Binding of Anti-Peroxidase Immunoglobulins in Bovine Colstrum, Publ: *Journal of Dairy Science,* vol./Iss: 80(12), pp. 3182-3187, Date: Dec. 1, 1998.
Author: Fujimoto, D.—CA Office Action, Title: Canadian Office Action cited in CA Application No. 2,448,607, Publ: *Canadian Office Action,* vol./Iss:, pp. 1-2, Date: Oct. 12, 2010.
Author: Japanese Patent Office, Title: Japanese Patent Application 2000-520153 Office Action as translated by Foreign Associate, Publ: *Japanese Office Action,* vol./Iss:, pp. 1-10, Date: Oct. 6, 2009.
Author: Japanese Publication, Title: Japanese Laid-Open Publication No. 9-107980 English Abstract only—of Japanese Patent Application 08-231415, Publ:, vol./Iss:, pp. 1-3, Date: Apr. 28, 1997.
Author:, Title: EPO Office Action cited in 02729092.3 (CYT0091EP), Publ: *EPO Office Action,* vol./Iss:, pp. 1-4, Date: Oct. 23, 2009.
Author:, Title: USPTO Office Action—cited in 09/189,657, Publ: *USPTO Office Action,* vol./Iss:, pp. 1-15, Date: Apr. 11, 2008.
Author:, Title: USPTO Office Action—cited in 12/250,126, Publ: *USPTO Office Action,* vol./Iss:, pp. 1-12, Date: Jun. 7, 2010.
Author:, Title: USPTO Office Action—cited in 12/708,326 (CYT-0110), Publ: *USPTO Office Action,* vol./Iss:, pp. 1-15, Date: Nov. 8, 2010.
Author:, Title: USPTO Office Action—cited in 11/016,204, Publ: *USPTO Office Action,* vol./Iss:, pp. 1-36, Date: Jul. 7, 2009.
Author: Van Den Pol, A. N., Title: Colloidal Gold and Biotin-Avidin Conjugates as Ultrasound Markers for Neural Antigens, Publ: *Quarterly Journal of Experimental Physiology,* vol./Iss:, pp. 1-33, Date: Jan. 1, 1984.

* cited by examiner

A

B

C

D

E

F

A

B

C

D

E

F

A

B

COLLOIDAL METAL COMPOSITIONS AND METHODS

Matter enclosed in heavy brackets [ ] appears in the original patent but forms no part of this reissue specification; matter printed in italics indicates the additions made by reissue.

RELATED APPLICATIONS

This application claims priority to Provisional Application Ser. No. 60/287,363 filed on Apr. 30, 2001.

FIELD OF THE INVENTION

The present invention relates to compositions and methods for generalized delivery of agents and delivery of agents to specific sites. In general, the present invention relates to colloidal metal compositions and methods for making and using such compositions.

BACKGROUND OF THE INVENTION

It has long been a goal of therapeutic treatment to find the magic bullet that would track to the site of need and deliver a therapeutic response without undue side effects. Many approaches have been tried to reach this goal. Therapeutic agents have been designed to take advantage of differences in active agents, such as hydrophobicity or hydrophilicity, or size of therapeutic particulates for differential treatment by cells of the body. Therapies exist that deliver therapeutic agents to specific segments of the body or to particular cells by in situ injection, and either use or overcome body defenses such as the blood-brain barrier, that limit the delivery of therapeutic agents.

One method that has been used to specifically target therapeutic agents to specific tissues or cells is delivery based on the combination of a therapeutic agent and a binding partner of a specific receptor. For example, the therapeutic agent may be cytotoxic or radioactive and when combined with a binding partner of a cellular receptor, cause cell death or interfere with genetic control of cellular activities once bound to the target cells. This type of delivery device requires having a receptor that is specific for the cell-type to be treated, an effective binding partner for the receptor, and an effective therapeutic agent. Molecular genetic manipulations have been used to overcome some of these problems.

Specific delivery of genetic sequences into exogenous cells or for over-expression of endogenous sequences are methods of great interest at the current time. Various techniques for inserting genes into cells are used. These techniques include precipitation, viral vectors, direct insertion with micropipettes and gene guns, and exposure of nucleic acid to cells. A widely used precipitation technique uses calcium phosphate to precipitate DNA to form insoluble particles. The goal is for at least some of these particles to become internalized within the host cells by generalized cellular endocytosis. This results in the expression of the new or exogenous genes. This technique has a low efficiency of entry of exogenous genes into cells with the resulting expression of the genes. The internalization of the genes is non-specific with respect to which cells are transfected because all exposed cells are capable of internalizing the exogenous genes since there is no reliance upon any particular recognition site for the endocytosis. This technique is used widely in vitro, but because of the lack of specificity of target cell selection and poor uptake by highly differentiated cells, its use in vivo is not contemplated. In addition, its use in vivo is limited by the insoluble nature of the precipitated nucleic acids.

A similar technique involves the use of DEAE-Dextran for transfecting cells in vitro. DEAE-Dextran is deleterious to cells and also results in non-specific insertion of nucleic acids into cells. This method is not advisable in vivo.

Other techniques for transfecting cells, or providing for the entry of exogenous genes into cells are also limited. Using viruses as vectors has some applicability for in vitro and in vivo introduction of exogenous genes into cells. There is always the risk that the presence of viral proteins will produce unwanted effects in an in vivo use. Additionally, viral vectors may be limited as to the size of exogenous genetic material that can be ferried into the cells. Repeated use of viral vectors raises an immunological response in the recipient and limits the times the vector can be used.

Exogenous gene delivery has also been used with liposome-entrapped nucleic acids. Liposomes are membrane-enclosed sacs that can be filled with a variety of materials, including nucleic acids. Liposome delivery does not provide for uniform delivery to cells because of uneven filling of the liposomes. Though liposomes can be targeted to specific cellular types if binding partners for receptors are included, liposomes suffer from breakage problems, and thus delivery is not specific.

Brute force techniques for inserting exogenous nucleic acids include puncturing cellular membranes with micropipettes or gene guns to insert exogenous DNA into a cell. These techniques work well for some procedures, but are not widely applicable. They are highly labor intensive and require very skilled manipulation of the recipient cell. These are not techniques that are simple procedures that work well in vivo. Electroporation, using electrical methods to change the permeability of the cellular membrane, has been successful for some in vitro therapies for insertion of genes into cells There have been some attempts at targeted delivery of DNA for specific cells that relied upon the presence of receptors for glycoproteins. The delivery system used polycations, such as polylysine, that were noncovalently bonded to DNA, and that were also covalently bonded to a ligand. Such use of covalently bonding of the polycations to a ligand does not allow for the disassembly of the delivery system once the cellular internalization mechanisms begin. This large complex, covalently bonded delivery system is very unlike the way nucleic acids are naturally found within cells.

Simple, efficient delivery systems for delivery of specific therapeutic agents to specific sites in the body for the treatment of diseases or pathologies or for the detection of such sites are not currently available. For example, current treatments for cancer include administration of chemotherapeutic agents and other biologically active factors such as cytokines and immune factors that impact the entire organism. The side effects include organ damage, loss of senses such as taste and feel, and hair loss. Such therapies provide treatment for the condition, but also require many adjunct therapies to treat the side effects.

What is needed are compositions and methods for delivery systems of agents that effect the desired cells or site. These delivery systems could be used for delivery to specific cells of agents of all types, including detection and therapeutic agents. What is also needed are delivery systems that do not cause unwanted side effects in the entire organism.

SUMMARY OF THE INVENTION

The present invention comprises compositions and methods for delivery systems of agents, including therapeutic compounds, pharmaceutical agents, drugs, detection agents, nucleic acid sequences and biological factors. In general, these vector compositions comprise a colloidal metal sol, derivatized PEG (polyethylene glycol) and an agent, and methods and compositions for making such colloidal metal sol compositions.

The vector compositions are particularly useful in detection or treatment of solid tumors. Preferred compositions of the present invention comprise vectors comprising colloidal metal sols, preferably gold metal sols, associated with derivatized-PEG, preferably thiol-PEG, and also comprise one or more agents that aid in specific targeting of the vector or have therapeutic effects or can be detected.

The present invention comprises methods of delivery by administering the compositions of the invention by known methods such as injection or orally, wherein the compositions are delivered to specific cells or organs. In one embodiment, the present invention comprises methods for treating diseases, such as cancer or solid tumors, by administering the compositions of the present invention comprising agents that are known for the treatment of such diseases. Another embodiment comprises vector compositions comprising derivatized PEG, TNF (Tumor Necrosis Factor) and anticancer agents, associated with colloidal metal particles. In another embodiment, the present invention comprises methods for gene therapy by administering the compositions of the present invention comprising agents that are used for gene therapy, such as oligonucleotides, antisense, vectors, ribozymes, DNA, RNA, sense oligonucleotides, and nucleic acids.

DETAILED DESCRIPTION

Figure 1:
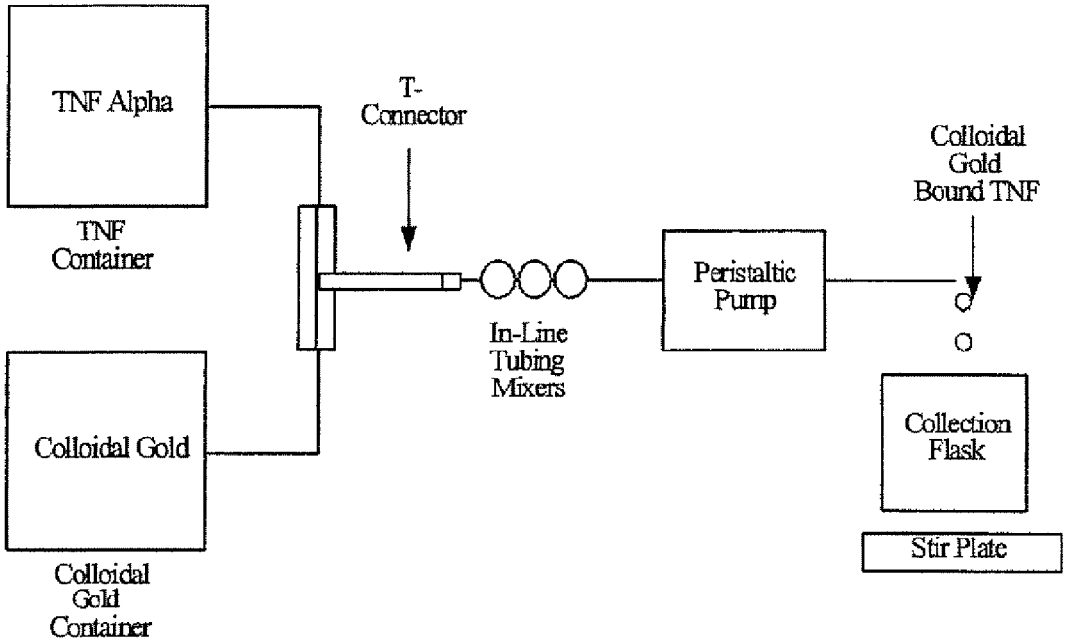
FIG. 1 is a schematic of a mixing apparatus used to prepare vectors.

The present invention comprises compositions and methods for the delivery of agents. The present invention also comprises methods for making the compositions and administering the compositions in vitro and in vivo. In general, the present invention contemplates compositions comprising metal sol particles associated with any or all of the following components alone or in combinations: active agents, detection agents, targeting molecules, integrating molecules, and one or more types PEG or derivatized PEGs.

The delivery of agents is used for detection or treatment of specific cells or tissues. For example, the present invention is used for imaging specific tissue, such as solid tumors. The delivery of agents is used for treatments of biological conditions, including, but not limited to, chronic and acute diseases, maintenance and control of the immune system and other biological systems, infectious diseases, vaccinations, hormonal maintenance and control, cancer, solid tumors and angiogenic states. Such delivery may be targeted to specific cells or cell types, or the delivery may be less specifically provided to the body, in methods that allow for low level release of the agent or agents in a nontoxic manner. Descriptions and uses of metal sol compositions are taught in U.S. Pat. No. 6,274,552; and related patent applications, U.S. patent application Ser. Nos. 09/808,809; 09/935,062; 09/189,748; 09/189,657,and 09/803,123; and U.S. Provisional Patent Applications 60/287,363, all of which are herein incorporated in their entireties.

The present invention is directed to methods and compositions comprising colloidal metals as vectors for delivery of agents. Specifically, preferred compositions are used in methods of treatment or detection comprising accumulation of one or more types of vectors in a solid tumor. Methods for treating solid tumors comprise administering colloidal metal sol compositions comprising PEG, preferably derivatized-PEG, more preferably, thiol-derivatized polyethylene glycols. Though not wishing to be bound by any particular theory, it is thought that use of such compositions results in the vector composition trafficking to and accumulating in tumors. In the absence of targeting molecules or active agents, a derivatized PEG colloidal metal vector traffics to the tumor and is sequestered there. All methods of administration are contemplated by the present invention, though the most preferable routes of administration are intravenous or oral. When administered, preferably intravenously or orally, the colloidal vectors are found in or associated with a tumor.

The compositions of the invention preferably comprise a colloidal metal sol, derivatized compounds and one or more agents. The agents may be biologically active agents that can be used in therapeutic applications or the agents may be agents that are useful in detection methods. In preferred embodiments, one or more agents are admixed, associated with or bound directly or indirectly to the colloidal metal. Admixing, associating and binding includes covalent and ionic bonds and other weaker or stronger associations that allow for long term or short term association of the derivatized-PEG, agents, and other components with each other and with the metal sol particles.

In yet another embodiment, the compositions also comprise one or more targeting molecules admixed, associated with or bound to the colloidal metal. The targeting molecule can be bound directly or indirectly to the metal particle. Indirect binding includes binding through molecules such as polylysines or other integrating molecules or any association with a molecule that binds to both the targeting molecule and either the metal sol or another molecule bound to the metal sol.

Any colloidal metal can be used in the present invention. Colloidal metal includes any water-insoluble metal particle or metallic compound dispersed in liquid water, a hydrosol or a metal sol. The colloidal metal may be selected from the metals in groups IA, IB, IIB and IIIB of the periodic table, as well as the transition metals, especially those of group VIII. Preferred metals include gold, silver, aluminum, ruthenium, zinc, iron, nickel and calcium. Other suitable metals also include the following in all of their various oxidation states: lithium, sodium, magnesium, potassium, scandium, titanium, vanadium, chromium, manganese, cobalt, copper, gallium, strontium, niobium, molybdenum, palladium, indium, tin, tungsten, rhenium, platinum, and gadolinium. The metals are preferably provided in ionic form, derived from an appropriate metal compound, for example the $Al^{3+}$, $Ru^{3+}$, $Zn^{2+}$, $Fe^{3+}$, $Ni^{2+}$ and $Ca^{2+}$ ions.

A preferred metal is gold, particularly in the form of $Al^{3+}$. An especially preferred form of colloidal gold is $HAuCl_4$. In one embodiment, the colloidal gold particles have a negative charge at an approximately neutral pH. It is thought that this negative charge prevents the attraction and attachment of other negatively charged molecules. In contrast, positively charged molecules are attracted to and bind to the colloidal gold particle. The colloidal gold is employed in the form of a sol which contains gold particles having a range of particle sizes, though a preferred size is a particle size of approximately 30 to 40 nm.

Another preferred metal is silver, particularly in a sodium borate buffer, having the concentration of between approximately 0.1% and 0.001%, and most preferably, approximately a 0.01% solution. Preferably, the color of such a colloidal silver solution is yellow and the colloidal particles range from 1 to 40 nm. Such metal ions may be present in the complex alone or with other inorganic ions.

The agent of the present invention can be any compound, chemical, therapeutic agent, pharmaceutical agent, drug, biological factors, fragments of biological molecules such as antibodies, proteins, lipids, nucleic acids or carbohydrates; nucleic acids, antibodies, proteins, lipids, nutrients, cofactors, nutriceuticals, anesthetic, detection agents or an agent that has an effect in the body. Such detection and therapeutic agents and their activities are known to those of ordinary skill in the art.

The following are non-limiting examples of some of the agents that can be used in the present invention. One type of agent that can be employed in the present invention includes biological factors including, but not limited to, cytokines, growth factors, fragments of larger molecules that have activity, neurochemicals, and cellular communication molecules. Examples of such agents include, but are not limited to, Interleukin-1 ("IL-1"), Interleukin-2 ("IL-2"), Interleukin-3 ("IL-3"), Interleukin-4 ("IL-4"), Interleukin-5 ("IL-5"), Interleukin-6 ("IL-6"), Interleukin-7 ("IL-7"), Interleukin-8 ("IL-8"), Interleukin-10 ("IL-10"), Interleukin-11 ("IL-11"), Interleukin-12 ("IL-12"), Interleukin-13 ("IL-13"), Interleukin-15 ("IL-15"), Interleukin-16 ("IL-16"), Interleukin-17 ("IL-17"), Interleukin-18 ("IL-18"), Type I Interferon, Type II Interferon, Tumor Necrosis Factor ("TNFα"), Transforming Growth Factor-α ("TGF-α"), Lymphotoxin, Migration Inhibition Factor, Granulocyte-Macrophage Colony-Stimulating Factor ("CSF"), Monocyte-Macrophage CSF, Granulocyte CSF, vascular epithelial growth factor ("VEGF"), Angiogenin, transforming growth factor-β ("TGF-β"), fibroblast growth factor, angiostatin, endostatin, GABA, and acetyl choline.

Another type of agent includes hormones. Examples of such hormones include, but are not limited to, growth hormone, insulin, glucagon, parathyroid hormone, luteinizing hormone, follicle stimulating hormone, luteinizing hormone releasing hormone, estrogen, testosterone, dihydrotestoerone, estradiol, prosterol, progesterone, progestin, estrone, other sex hormones, and derivatives and analogs of hormones.

Yet another type of agent includes pharmaceuticals. Any type of pharmaceutical agent can be employed in the present invention. For example, antiinflammatory agents such as steroids and nonsteroidal antiinflammatory agents, soluble receptors, antibodies, antibiotics, analgesics, angiogenic and anti-angiogenic agents, and COX-2 inhibitors, can be employed in the present invention. Chemotherapeutic agents are of particular interest in the present invention. Nonlimiting examples of such agents include taxol, paclitaxel, taxanes, vinblastin, vincristine, doxorubicin, acyclovir, cis-platin and tacrine.

Immunotherapy agents are also of particular interest in the present invention. Nonlimiting examples of immunotherapy agents, include inflammatory agents, biological factors, immune regulatory proteins, and immunotherapy drugs, such as AZT and other derivatized or modified nucleotides. Small molecules can also be employed as agents in the present invention.

Another type of agent includes nucleic acid-based materials. Examples of such materials include, but are not limited to, nucleic acids, nucleotides, DNA, RNA, tRNA, mRNA, sense nucleic acids, antisense nucleic acids, ribozymes, DNAzymes, protein/nucleic acid compositions, SNPs, oligonucleotides, vectors, viruses, plasmids, transposons, and other nucleic acid constructs known to those skilled in the art.

Other agents that can be employed in the invention include, but are not limited to, lipid A, phospholipase A2, endotoxins, staphylococcal enterotoxin B and other toxins, heat shock proteins, carbohydrate moieties of blood groups, Rh factors, cell surface receptors, antibodies, cancer cell specific antigens; such as MART, MAGE, BAGE, and HSPs (Heat Shock Proteins), radioactive metals or molecules, detection agents, enzymes and enzyme co-factors.

Of particular interest are detection agents such as dyes or radioactive materials that can be used for visualizing or detecting the sequestered colloidal metal vectors. Fluorescent, chemiluminescent, heat sensitive, opaque, beads, magnetic and vibrational materials are also contemplated for use as detectable agents that are associated or bound to colloidal metals in the compositions of the present invention.

Other examples of agents and organisms that are affected by treatment methods of the present invention are found in the following table. This table is not limiting in that other agents, such as the pharmaceutical equivalents of the following agents, are contemplated by the present invention.

TABLE I

| Organisms and Selected Active Agents | |
|---|---|
| BACTERIA | |
| *Mycobacterium tuberculosis* | Isoniazid, rifampin, ethambutol, pyrazinamide, streptomycin, clofazimine, rifabutin, fluoroquinolones such as ofloxacin and sparfloxacin |
| *Mycobacterium avium* | Rifabutin, rifampin, azithromycin, clarithromycin, fluoroquinolones |
| *Mycobacterium leprae* | Dapsone |
| *Chlamydia trachomatis* | Tetracycline, doxycyline, erythromycin, ciprofloxacin |
| *Chlamydia pneumoniae* | Doxycycline, erythromycin |
| *Listeria monocytogenes* | Ampicillin |
| FUNGI | |
| *Candida albicans* | Amphotericin B, ketoconazole, fluconazole |
| *Cryptococcus neoformans* | Amphotericin B, ketoconazole, fluconazole |
| PROTOZOA | |
| *Toxoplasma gondii* | Pyrimethamine, sulfadiazine, clindamycin, azithromycin, clarithromycin, atovaquone |
| *Pneumocystis carinii* | Pentamidine, atovaquone |
| *Cryptosporidium* sp. | Paromomycin, diclazaril |
| VIRUS | |
| Herpes simplex virus type 1 | Acyclovir, trifluorouridine and other and type 2 antiviral nucleoside analogs, foscornat, antisense oligonucleotides, and triplex-specific DNA sequences |
| Cytomegalovirus | Foscarnet, ganciclovir |
| HIV | AZT, DDI, DDC, foscarnat, viral protease inhibitors, peptides, antisense oligonucleotides, triplex and other nucleic acid sequences |
| Influenza virus types A & B | Ribavirin |
| Respiratory syncytial virus | Ribavirin |
| Varizella zoster virus | Acyclovir |

Targeting molecules are also components of compositions of the present invention. One or more targeting molecules may be directly or indirectly attached, bound or associated with the colloidal metal. These targeting molecules can be directed to specific cells or cell types, cells derived from a specific embryonic tissue, organs or tissues. Such targeting molecules include any molecules that are capable of selectively binding to specific cells or cell types. In general, such targeting molecules are one member of a binding pair and as such, selectively bind to the other member. Such selectivity may be achieved by binding to structures found naturally on cells, such as receptors found in cellular membranes, nuclear membranes or associated with DNA. The binding pair member may also be introduced synthetically on the cell, cell type, tissue or organ. Targeting molecules also include receptors or parts of receptors that may bind to molecules found in the cellular membranes or free of cellular membranes, ligands, antibodies, antibody fragments, enzymes, cofactors, substrates, and other binding pair members known to those skilled in the art. Targeting molecules may also be capable of binding to multiple types of binding partners. For example, the targeting molecule may bind to a class or family of receptors or other binding partners. The targeting molecule may also be an enzyme substrate or cofactor capable of binding several enzymes or types of enzymes.

Specific examples of targeting molecules include, but are not limited to, Interleukin-1 ("IL-1"), Interleukin-2 ("IL-2"), Interleukin-3 ("IL-3"), Interleukin-4 ("IL-4"), Interleukin-5 ("IL-5"), Interleukin-6 ("IL-6"), Interleukin-7 ("IL-7"), Interleukin-8 ("IL-8"), Interleukin-10 ("IL-10"), Interleukin-11 ("IL-11"), Interleukin-12 ("IL-12"), Interleukin-13 ("IL-13"), Interleukin-15 ("IL-15"), Interleukin-16 ("IL-16"), Interleukin-17 ("IL-17"), Interleukin-18 ("IL-18"), lipid A, phospholipase A2, endotoxins, staphylococcal enterotoxin B and other toxins, Type I Interferon, Type II Interferon, Tumor Necrosis Factor ("TNFα"), Transforming Growth Factor-α "TGF-α"), Lymphotoxin, Migration Inhibition Factor, Granulocyte-Macrophage Colony-Stimulating Factor ("CSF"), Monocyte-Macrophage CSF, Granulocyte CSF, vascular epithelial growth factor ("VEGF"), Angiogenin, transforming growth factor-β ("TGF-β"), carbohydrate moieties of blood groups, Rh factors, fibroblast growth factor and other inflammatory and immune regulatory proteins, hormones, such as growth hormone, insulin, glucagon, parathyroid hormone, luteinizing hormone, follicle stimulating hormone, and luteinizing hormone releasing hormone, cell surface receptors, antibodies, nucleic acids, nucleotides, DNA, RNA, sense nucleic acids, antisense nucleic acids, cancer cell specific antigens, MART, MAGE, BAGE, and HSPs (Heat Shock Proteins), mutant p53; tyrosinase; antoimmune antigens; receptor proteins, glucose, glycogen, phospholipids, and monoclonal and/or polyclonal antibodies, basic fibroblast growth factor, enzymes, cofactors and enzyme substrates.

The integrating molecules used in the present invention can either be specific binding integrating molecules, such as members of a binding pair, or can be nonspecific binding integrating molecules that bind less specifically. An integrating molecule is defined by its function of providing a site for binding or associating two entities. One entity can comprise a metal sol particle, and the other entity can comprise one or more active agents or one or more targeting molecules, or both or combinations thereof. The compositions of the present invention can comprise one or more integrating molecules.

An example of a nonspecific binding-integrating molecule is polycationic molecules such as polylysine or histones that are useful in binding nucleic acids. Polycationic molecules are known to those skilled in the art and include, but are not limited to, polylysine, protamine sulfate, histones or asialoglycoproteins. The present invention also contemplates the use of synthetic molecules that provide for binding one or more entities to the metal particles.

Specific binding-integrating molecules comprise any members of binding pairs that can be used in the present invention. Such binding pairs are known to those skilled in the art and include, but are not limited to, antibody-antigen pairs, enzyme-substrate pairs, receptor-ligand pairs, and streptavidin-biotin. In addition to such known binding pairs, novel binding pairs may be specifically designed. A characteristic of binding pairs is the binding between the two members of the binding pair. Another desired characteristic of the binding partners is that one member of the pair is capable of binding or being bound to one or more of an agent or a targeting molecule, and the other member of the pair is capable of binding to the metal particle.

Another component of the compositions of the present invention comprises glycol compounds, preferably polyethylene glycol (PEG), more preferably derivatized PEG. The present invention comprises compositions comprising derivatized PEG, wherein the PEG is 5,000 to 30,000 MW. Derivatized PEG compounds are commercially available from sources such as Shearwater Corporation, Huntsville, Ala. PEG compounds may be difunctional or monofunctional, such as methoxy-PEG (mPEG). Activated derivatives of linear and branched PEGs are available in a variety of molecular weights. As used herein, the term "derivatized PEG(s)" or "PEG derivative(s)" means any polyethylene glycol molecule that has been altered with either addition of functional groups, chemical entities, or addition of other PEG groups to provide branches from a linear molecule. Such derivatized PEGs can be used for conjugation with biologically active compounds, preparation of polymer grafts, or other functions provided by the derivatizing molecule.

One type of PEG derivative is a polyethylene glycol molecule with primary amino groups at one or both of the termini. A preferred molecule is methoxy PEG with an amino group on one terminus. Another type of PEG derivative includes electrophilically activated PEG. These PEGs are used for attachment of PEG or methoxy PEG (mPEG), to proteins, liposomes, soluble and insoluble polymers and a variety of molecules. Electrophilically active PEG derivatives include succinimide of PEG propionic acid, succinimide of PEG butanoate acid, multiple PEGs attached to hydroxysuccinimide or aldehydes, mMPEG double esters (mPEG-CM-HBA-NHS), MPEG benzotriazole carbonate, and MPEG propionaldehyde, niPEG acetaldehyde diethyl acetal.

A preferred type of derivatized PEG comprises thiol derivatized PEGs, or sulfhydryl-selective PEGs. Branched, forked or linear PEGs can be used as the PEG backbone that has a molecular weight range of 5,000 to 40,000 mw. Preferred thiol derivatized PEGs comprise PEG with maleimide functional group to which a thiol group can be conjugated. A preferred thiol-PEG is methoxy-PEG-maleimide, with PEG mw of 5,000 to 40,000.

Use of heterofunctional PEGs, as a derivatized PEG, is also contemplated by the present invention. Heterofunctional derivatives of PEG have the general structure X-PEG-Y. When the X and Y are functional groups that provide conjugation capabilities, many different entities can be bound on either or both termini of the PEG molecule. For example, vinylsulfone or maleimide can be X and an NHS ester can be Y. For detection methods, X and/or Y can be fluorescent molecules, radioactive molecules, luminescent molecules or other detectable labels. Heterofunctional PEG or monofunctional PEGs can be used to conjugate one member of a binding pair, such as PEG-biotin, PEG-Antibody, PEG-antigen, PEG-receptor, PEG-enzyme or PEG-enzyme substrate. PEG can also be conjugated to lipids such as PEG-phospholipids.

One or more agents of the compositions of the present invention can be bound directly to the colloidal metal particles or can be bound indirectly to the colloidal metal through one or more integrating molecules. One method of preparing colloidal metal sols of the present invention uses the method described by Horisberger, (1979), which is incorporated by reference herein. In embodiments where an integrating molecule is employed, the integrating molecule is bound to, admixed or associated with the metal sol. The agent may be bound to, admixed or associated with the integrating molecule prior to the binding, admixing or associating of the integrating molecule with the metal, or may be bound, admixed or associated after the binding of the integrating molecule to the metal.

General methods for binding agents to metal sols comprise the following steps. A solution of the agent is formed in a buffer or solvent, such as deionized water (di$H_2O$). The appropriate buffer or solvent will depend upon the agent to be bound. Determination of the appropriate buffer or solvent for a given agent is within the level of skill of the ordinary artisan. Determining the pH necessary to bind an optimum amount of agent to metal sol is known to those skilled in the art. The amount of agent bound can be determined by quantitative methods for determining proteins, therapeutic agents or detection agents, such as ELISA or spectrophotometric methods. Where integrating molecules are employed in the present invention, the binding pH and saturation level of the integrating molecule is also considered in preparing the compositions. For example, where the integrating molecule is a member of a binding pair, such as Streptavidin-biotin, the binding pH for streptavidin or biotin is determined and the concentration of the streptavidin or biotin bound can also determined.

When the vector composition comprises an integrating molecule, the agent may be bound to a member of the binding pair which is functioning as an integrating molecule, such as biotin, by conventional methods known in the art. The biotinylated agent can then be added to the colloidal gold composition comprising the integrating molecule, streptavidin. The biotin binds specifically to the streptavidin providing an indirect bond between the colloidal gold and the active agent.

One method of binding an agent to metal sols comprises the following steps, though for clarity purposes only, the methods disclosed refer to binding an agent, TNF, to a metal sol, colloidal gold. An apparatus was used that allows interaction between the particles in the colloidal gold sol and TNF in a protein solution. A schematic representation of the apparatus is shown in FIG. 1. This apparatus maximizes the interaction of unbound colloidal gold particles with the protein to be bound, TNF, by reducing the mixing chamber to a small volume. This apparatus enables the interaction of large volumes of gold sols with large volumes of TNF to occur in the small volume of a T connector. In contrast, adding a small volume of protein to a large volume of colloidal gold particles is not a preferred method to ensure uniform protein binding to the gold particles. Nor is the opposite method of adding small volumes of colloidal gold to a large volume of protein. Physically, the colloidal gold particles and the protein, TNF are forced into a T-connector by a single peristaltic pump that draws the colloidal gold particles and the TNF protein from two large reservoirs. To further ensure proper mixing, an in-line mixer is placed immediately down stream of the T-connector. The mixer vigorously mixes the colloidal gold particles with TNF, both of which are flowing through the connector at a preferable flow rate of approximately 1 L/min.

Prior to mixing with the agent, the pH of the gold sol is adjusted to pH 8-9 using 1 N NaOH. Highly purified, lyophilized recombinant human TNF is reconstituted and diluted in 3 mM Tris. Before adding either the sol or TNF to their respective reservoirs, the tubing connecting the containers to the T-connector is clamped shut. Equal volumes of colloidal gold sol and the TNF solution are added to the appropriate reservoirs. Preferred concentrations of agent in the solution range from approximately 0.01 to 15 μg/ml, and can be altered depending on the ratio of the agent to metal sol particles. Preferred concentrations of TNF in the solution range from 0.5 to 4 μg/ml and the most preferred concentration of TNF for the TNF-colloidal gold composition is 0.5 μg/ml.

Once the solutions are properly loaded into their respective reservoirs, the peristaltic pump is turned on, drawing the agent solution and the colloidal gold solution into the T-connector, through the in-line mixer, through the peristaltic pump and into a collection flask. The mixed solution is stirred in the collection flask for an additional hour of incubation.

In compositions comprising PEG, whether derivatized or not, the methods for making such compositions comprise the following steps, though for clarity purposes only, the methods disclosed refer to adding PEG thiol to a metal sol composition. Any PEG, derivatized PEG composition or any sized PEG compositions or compositions comprising several different PEGs, can be made using the following steps. Following the 1-hour incubation taught above, a thiol derivatized polyethylene glycol (PEG) solution is added to the colloidal gold/TNF sol. The present invention contemplates use of any sized PEG with any derivative group, though preferred derivatized PEGs include mPEG-OPSS/5,000, thiol-PEG-thiol/3,400, mPEG-thiol 5000, and mPEG thiol 20,000 (Shearwater Polymers, Inc.). A preferred PEG is mPEG-thiol 5000 at a concentration of 150 μg/ml in water, pH 5-8. Thus, a 10% v/v of the PEG solution is added to the colloidal gold-TNF solution. The gold/TNF/PEG solution is incubated for an additional hour.

The colloidal gold/TNF/PEG solution is subsequently ultrafiltered through a 50K MWCO diafiltration cartridge. The 50K retentate and permeate are measured for TNF concentration by ELISA to determine the amount of TNF bound to the gold particles.

The compositions of the present invention can be administered to in vitro and in vivo systems. In vivo administration may include direct application to the target cells or such routes of administration, including but not limited to formulations suitable for oral, rectal, transdermal, ophthalmic, (including intravitreal or intracameral) nasal, topical (including buccal and sublingual), vaginal or parenteral (including subcutaneous, intramuscular, intravenous, intradermal, intratracheal, and epidural) administration. A preferred method comprising administering, via oral or injection routes, an effective amount of a composition comprising vectors of the present invention.

The formulations may conveniently be presented in unit dosage form and may be prepared by conventional pharmaceutical techniques. Pharmaceutical formulation compositions are made by bringing into association the metal sol vectors and the pharmaceutical carrier(s) or excipient(s). In general, the formulations are prepared by uniformly and intimately bringing into association the compositions with liquid carriers or finely divided solid carriers or both, and then, if necessary, shaping the product.

Preferred methods of use of the compositions of the present invention comprise targeting the vectors to tumors. Preferred vector compositions comprise metal sol particles, agents and PEG or derivatized PEG compositions for delivery to a tumor for therapeutic effects on the tumor or organism or detection of tumors. Such vector compositions may further comprise targeting and/or integrating molecules. Still other preferred vector compositions comprise metal sol particles, radioactive or cytotoxic agents and PEG or derivatized PEG compositions for delivery of radiation therapies to tumors. Historically, radioactive colloidal gold was used as a cancer therapy, principally for the treatment of liver cancer due to the anticipated uptake of colloidal gold by the liver cells. Compositions comprising derivatized PEG, preferably PEG thiol, in combination with radioactive colloidal metal particles are used to treat or identify tumors. Alternatively, a vector composition comprising a radioactive moiety coupled to a protein that is bound to colloidal metal, and further comprising derivatized PEG, preferably PEG-thiol, forming a radioactive vector, is used to treat tumors. The radioactive vector composition of the present invention is injected intravenously and traffics to the tumor and is not significantly taken up by the liver. In both compositions, it is believed that the ability of the PEG thiol to concentrate the radioactive therapy in the tumor increases treatment efficacy while reducing treatment side effects.

Other preferred vector compositions comprise metal sol particles and PEG, preferably PEG derivatives, for use in methods comprising administering the compositions for in vivo imaging and detection of tumors. The compositions may further comprise agents that aid in the detection and imaging methods. For example, the agents include, but are not limited to, radioactive, radiation sensitive or reactive, such as light or heat reactive compounds, chemiluminescent or luminescent agents or other agents used for detection purposes. Methods of detection include, but are not limited to NMR, CAT or PET scans, visual examination, colorimetric, radiation detection methods, spectrophotometric, and protein, nucleic acid, polysaccharide or other biological agent detection methods.

The present invention comprises compositions for use in methods for delivery of exogenous nucleic acids or genetic material into cells. The exogenous genetic material may be targeted to specific cells using targeting molecules that are capable of recognizing the specific cells or specifically targeted to tumors using compositions comprising PEG or derivatized PEG. For example, the targeting molecule is a binding partner for a specific receptor on the cells, and after binding, the entire composition may be internalized within the cells. The binding of the vector composition may activate cellular mechanisms that alter the state of the cell, such as activation of secondary messenger molecules within the cell. Thus, in a mixture of different cell types, the exogenous nucleic acids are delivered to cells having the selected receptor and cells lacking the receptor are unaffected.

The present invention comprises compositions and methods for the transfection of specific cells, in vitro or in vivo, for insertion or application of agents. One embodiment of such a composition comprises nucleic acid bound to polycations (nonspecific binding-integrating molecules) that are bound to colloidal metals. A preferred embodiment of the present invention comprises colloidal gold as a platform that is capable of binding targeting molecules and nucleic acid agents to create a targeted gene delivery vector that employs receptor-mediated endocytosis of cells to achieve transfection. In a more preferred embodiment, the targeting molecule is a cytokine and the agent is genetic material such as DNA or RNA. This embodiment may also comprise integrating molecules such as polycations to which the genetic material is bound or associated.

In the present invention, the methods comprise the preparation of gene delivery vectors and delivery of the targeted gene delivery vector to the cells for transfection or therapeutic effects. It is contemplated in the present invention that the nucleic acids of the compositions may be internalized and used as detection agents or for genetic therapeutic effects, or the nucleic acids can be translated and expressed by the cell. The expression products can be any known to those skilled in the art and includes but is not limited to functioning proteins, production of cellular products, enzymatic activity, export of cellular products, production of cellular membrane components, or nuclear components. The methods of delivery to the targeted cells may be such methods as those used for in vitro techniques such as with cellular cultures, or those used for in vivo administration. In vivo administration may include direct application to the cells or such routes of administration as used for humans, animals or other organism, preferably intravenous or oral administration. The present invention also contemplates cells that have been altered by the compositions of the present invention and the administration of such cells to other cells, tissues or organisms, in in vitro or in vivo methods.

The present invention comprises compositions and methods for enhancing an immune response and increasing vaccine efficacy through the simultaneous or sequential targeting of specific immune cells using compositions directed to specific immune components. The compositions can also be used in methods for imaging or detecting immune cells. These methods comprise vector compositions that are capable of effecting the immune system, and include colloidal metals associated with at least one of the following components, targeting molecules, agents, integrating molecules, one or more types of PEG or derivatized PEGs. The compositions may also comprise specific immune components, such as cells including, but not limited to, antigen presenting cells (APCs), such as macrophages and dendritic cells, and lymphocytes, such as B cells and T cells, which have been or are individually effected by one or more component-specific immunostimulating agents.

Examples of component-specific immunostimulating molecules include, but are not limited to, Interleukin-1 ("IL-1"), Interleukin-2 ("IL-2"), Interleukin-3 ("IL-3"), Interleukin-4 ("IL-4"), Interleukin-5 ("IL-5"), Interleukin-6 ("IL-6"), Interleukin-7 ("IL-7"), Interleukin-8 ("IL-8"), Interleukin-10 ("IL-10"), Interleukin-11 ("IL-11"), Interleukin-12 ("IL-12"), Interleukin-13 ("IL-13"), lipid A, phospholipase A2, endotoxins, staphylococcal enterotoxin B and other toxins, Type I Interferon, Type II Interferon, Tumor Necrosis Factor ("TNF-α"), Transforming Growth Factor-β("TGF-β" Lymphotoxin, Migration Inhibition Factor, Granulocyte-Macrophage Colony-Stimulating Factor ("CSF"), Monocyte-Macrophage CSF, Granulocyte CSF, vascular epithelial growth factor ("VEGF"), Angiogenin, transforming growth factor ("TGF-α"), heat shock proteins, carbohydrate moieties of blood groups, Rh factors, fibroblast growth factor, and other inflammatory and immune regulatory proteins, nucleotides, DNA, RNA, mRNA, sense, antisense, cancer cell specific antigens; such as MART, MAGE, BAGE; flt3 ligand/receptor system; B7 family of molecules and receptors; CD 40 ligand/receptor; and immunotherapy drugs, such as AZT; and angiogenic and anti-angiogenic drugs, such as angiostatin, endostatin, and basic fibroblast growth factor, or vascular endothelial growth factor (VEGF).

An especially preferred embodiment provides methods for activation of the immune response using vector compositions comprising agents comprising a specific antigen in combination with a component-specific immunostimulating agent. As used herein, component-specific immunostimulating agent means an agent that is specific for a component of the immune system, such as a B or T cell, and that is capable of affecting that component, so that the component has an activity in the immune response. The component-specific immunostimulating agent may be capable of affecting several different components of the immune system, and this capability may be employed in the methods and compositions of the present invention. The agent may be naturally occurring or can be generated or modified through molecular biological techniques or protein receptor manipulations.

The activation of the component in the immune response may result in a stimulation or suppression of other components of the immune response, leading to an overall stimulation or suppression of the immune response. For ease of expression, stimulation of immune components is described herein, but it is understood that all responses of immune components are contemplated by the term stimulation, including but not limited to stimulation, suppression, rejection and feedback activities.

The immune component that is effected may have multiple activities, leading to both suppression and stimulation or initiation or suppression of feedback mechanisms. The present invention is not to be limited by the examples of immunological responses detailed herein, but contemplates component-specific effects in all aspects of the immune system.

The activation of each of the components of the immune system may be simultaneous, sequential, or any combination thereof. In one embodiment of a method of the present invention, multiple component-specific immunostimulating agents are administered simultaneously. In this method, the immune system is simultaneously stimulated with multiple separate preparations, each containing a vector composition comprising a component-specific immunostimulating agent. Preferably, the vector composition comprises the component-specific immunostimulating agent associated with colloidal metal. More preferably, the composition comprises the component-specific immunostimulating agent associated with colloidal metal of one sized particle or of different sized particles and an antigen. Most preferably, the composition comprises the component-specific immunostimulating agent associated with colloidal metal of one sized particle or of differently sized particles, antigen and PEG or PEG derivatives.

Component-specific immunostimulating agents provides a specific stimulatory, up regulation, effect on individual immune components. For example, Interleukin-1β (IL-1β) specifically stimulates macrophages, while TNF-α (Tumor Necrosis Factor alpha) and Flt-3 ligand specifically stimulate dendritic cells. Heat killed Mycobacterium butyricum and Interleukin-6 (IL-6) are specific stimulators of B cells, and Interleukin-2 (IL-2) is a specific stimulator of T cells. Vector compositions comprising such component-specific immunostimulating agents provide for specific activation of macrophages, dendritic cells, B cells and T cells, respectively. For example, macrophages are activated when a vector composition comprising the component-specific immunostimulating agent IL-1β is administered. A preferred composition is IL-1β in association with colloidal metal, and a most preferred composition is IL-1β in association with colloidal metal and an antigen to provide a specific macrophage response to that antigen. Vector compositions can further comprise targeting molecules, integrating molecules, PEGs or derivatized PEGs.

Many elements of the immune response may be necessary for an effective immune response to an antigen. An embodiment of a method of simultaneous stimulation is to administer four separate preparations of compositions of component-specific immunostimulating agents comprising 1) IL-1β for macrophages, 2) TNF-α and Flt-3 ligand for dendritic cells, 3) IL-6 for B cells, and 4) IL-2 for T cells. Each component-specific immunostimulating agent vector composition may be administered by any routes known to those skilled in the art, and all may use the same route or different routes, depending on the immune response desired.

In another embodiment of the methods and compositions of the present invention, the individual immune components are activated sequentially. For example, this sequential activation can be divided into two phases, a primer phase and an immunization phase. The primer phase comprises stimulating APCs, preferably macrophages and dendritic cells, while the immunization phase comprises stimulating lymphocytes, preferably B cells and T cells. Within each of the two phases, activation of the individual immune components may be simultaneous or sequential. For sequential activation, a preferred method of activation is administration of vector compositions that cause activation of macrophages followed by dendritic cells, followed by B cells, followed by T cells. A most preferred method is a combined sequential activation comprising the administration of vector compositions which cause simultaneous activation of the macrophages and dendritic cells, followed by the simultaneous activation of B cells and T cells. This is an example of methods and compositions of multiple component-specific immunostimulating agents to initiate several pathways of the immune system.

The methods and compositions of the present invention can be used to enhance the effectiveness of any type of vaccine. The present methods enhance vaccine effectiveness by targeting specific immune components for activation. Vector compositions comprising at least component-specific immunostimulating agents in association with colloidal metal and antigen are used for increasing the contact between antigen and the specific immune component, such as macrophages, B or T cells. Examples of diseases for which vaccines are currently available include, but are not limited to, cholera, diphtheria, Haemophilus, hepatitis A, hepatitis B, influenza, measles, meningitis, mumps, pertussis, small pox, pneumococcal pneumonia, polio, rabies, rubella, tetanus, tuberculosis, typhoid, Varicella-zoster, whooping cough, and yellow fever.

The combination of routes of administration and the vector compositions for delivering the antigen to the immune system is used to create the desired immune response. The present invention also comprises methods and compositions comprising various compositions of packaging systems, such as liposomes, microcapsules, or microspheres, that can provide long-term release of immune stimulating vector compositions. These packaging systems act as internal depots for holding antigen and slowly releasing antigen for immune system activation. For example, a liposome may be filled with a vector composition comprising the agents of an antigen and component-specific immunostimulating agent, bound to or associated with a colloidal metal. Additional combinations are colloidal gold particles studded with agents such as viral particles which are the active vaccine candidate or are packaged to contain DNA for a putative vaccine. The vector may also comprise one or more targeting molecules, such as a cytokine, integrating molecules and PEG derivatives, and the vector is then used to target the virus to specific cells. Furthermore, one could use a fusion protein vaccine, which targets two or more potential vaccine candidates, and provide a vector composition vaccine that provides protection against two or more infectious microorganisms. The compositions may also include immunogens, which have been chemically modified by the addition of polyethylene glycol which may release the material slowly.

The compositions comprising a metal particle and the agents comprising one or more antigens and one or more component-specific immunostimulating agents, and one or more of integrating and targeting molecules and PEG or derivatives of PEG, may be packaged in a liposome or a biodegradable polymer. The vector composition is slowly released from the liposome or biodegradable polymer and is recognized by the immune system as foreign and the specific component to which the component-specific immunostimulating agent is directed activates or suppresses the immune system. For example, the cascade of the immune response is activated more quickly by the presence of the component-specific immunostimulating agent and the immune response is generated more quickly and more specifically.

Other methods and compositions contemplated in the present invention include using compositions of metal particles and agents comprising antigens and component-specific immunostimulating agents, which may also comprise integrating and targeting molecules, in which the colloidal metal particles have different sizes. The compositions may further comprise PEG or derivatives of PEG. Sequential administration of component-specific immunostimulating agents may be accomplished in a one dose administration by use of differently sized colloidal metal particles. One dose would include multiple independent component-specific immunostimulating agents an antigen and the combination could be associated with a differently sized or the same sized colloidal metal particle. Thus, simultaneous administration would provide sequential activation of the immune components to yield a more effective vaccine and more protection for the population. Other types of such single-dose administration with sequential activation could be provided by combinations of differently sized or same sized colloidal metal vector compositions and liposomes or biodegradable polymers, or liposomes or biodegradable polymers filled with differently sized or same-sized colloidal metal vector compositions.

Use of such vaccination systems as described above are important in providing vaccines that can be administered in one dose. One dose administration is important in treating animal populations such as livestock or wild populations of animals. One dose administration is vital in treatment of populations for whom healthcare is rarely accessible such as the poor, homeless, rural residents or persons in developing countries that have inadequate health care. Many persons, in all countries, do not have access to preventive types of health care, such as vaccination. The reemergence of infectious diseases, such as tuberculosis, has increased the demand for vaccines that can be given once and still provide long-lasting, effective protection. The compositions and methods of the present invention provide such effective protection.

The methods and compositions of the present invention can also be used to treat diseases in which an immune response occurs, by stimulating or suppressing components that are a part of the immune response. Examples of such diseases include, but are not limited to, Addison's disease, allergies, anaphylaxis, Bruton's syndrome, cancer, including solid and blood borne tumors, eczema, Hashimoto's thyroiditis, polymyositis, dermatomyositis, type 1 diabetes mellitus, acquired immune deficiency syndrome, transplant rejection, such as kidney, heart, pancreas, lung, bone, and liver transplants, Graves' disease, polyendocrine autoimmune disease, hepatitis, microscopic polyarteritis, polyarteritis nodosa, pemphigus, primary biliary cirrhosis, pernicious anemia, coeliac disease, antibody-mediated nephritis, glomerulonephritis, rheumatic diseases, systemic lupus erthematosus, rheumatoid arthritis, seronegative spondylarthritides, rhinitis, sjogren's syndrome, systemic sclerosis, sclerosing cholangitis, Wegener's granulomatosis, dermatitis herpetiformis, psoriasis, vitiligo, multiple sclerosis, encephalomyelitis, Guillain-Barre syndrome, myasthenia gravis, Lambert-Eaton syndrome, sclera, episclera, uveitis, chronic mucocutaneous candidiasis, urticaria, transient hypogammaglobulinemia of infancy, myeloma, X-linked hyper IgM syndrome, Wiskott-Aldrich syndrome, ataxia telangiectasia, autoimmune hemolytic anemia, autoimmune thrombocytopenia, autoimmune neutropenia, Waldenstrom's macroglobulinemia, amyloidosis, chronic lymphocytic leukemia, and non-Hodgkin's lymphoma.

The vector compositions of the present invention comprise agents comprising component-specific immunostimulating agents. A composition may comprise one component-specific immunostimulating agent or multiple component-specific immunostimulating agents. Preferred embodiments of the vector compositions comprise agents comprising component-specific immunostimulating agents in association with colloidal metals. More preferred embodiments comprise compositions comprising agents comprising one or more antigens and component-specific immunostimulating agents in association with colloidal metals and at least one of the following, PEG or derivatives of PEG, integrating molecules and targeting molecules for specifically targeting the effect of the component-specific immunostimulating agents, including, but not limited to, antigens, receptor molecules, nucleic acids, pharmaceuticals, chemotherapy agents, and carriers. The compositions of the present invention may be delivered to the immune components in any manner. In one embodiment, the agents, comprising an antigen and a component-specific immunostimulating agent, are bound to a colloidal metal in such a manner that a colloidal metal particle is associated with both the antigen and the immunostimulating agent.

The present invention includes presentation of agents such as antigen and component-specific immunostimulating agents in a variety of different delivery platforms or carrier combinations. For example, a preferred embodiment includes administration of a vector composition comprising a metal colloid particle bound to agents such as an antigen and component-specific immunostimulating agents in a liposome or biodegradable polymer carrier. Additional combinations are colloidal gold particles associated with agents such as viral particles which are the vaccine antigen or which are viable viral particles containing nucleic acids that produce antigens for a vaccine. The vector compositions may also comprise targeting molecules such as a cytokine or a selected binding pair member which is used to target the virus to specific cells, and further comprises other elements taught herein such as integrating molecules or PEG or PEG derivatives Such embodiments provide for a vaccine preparation that slowly releases antigen to the immune system for a prolonged response. This type of vaccine is especially beneficial for one-time administration of vaccines. All types of carriers, including but not limited to liposomes and microcapsules are contemplated in the present invention.

Toxicity Reduction and Vaccine Administration

The present invention comprises compositions and methods for administering factors that, when the factors are present in higher than normal concentrations, are toxic to a human or animal. Generally, the compositions according to the present invention comprise a vector composition that is an admixture of a colloidal metal in combination with an agent which is toxic to a human or animal when the agent is found in higher than normal concentration, or is in an unshielded form that allows for greater activity than in a shielded form, or is found in a site where it is not normally found. When the vector composition is administered to a human or animal, the agent is less harmful or less toxic or non-toxic to the human or animal than when the agent is provided alone without the colloidal metal vector composition. The compositions optionally include a pharmaceutically-acceptable carrier, such as an aqueous solution, or excipients, buffers, antigen stabilizers, or sterilized carriers. Also, oils, such as paraffin oil, may optionally be included in the composition. The vector compositions may further comprise PEG or derivatives of PEG.

The compositions of the present invention can be used to vaccinate a human or animal against agents that are toxic when injected. In addition, the present invention can be used to treat certain diseases with cytokines or growth factors by administering the compositions comprising agents such as cytokines or growth factors. By admixing the agents with the colloidal metal before administering the agents to the human or animal, the toxicity of the agent is reduced or eliminated thereby allowing the factor to exert its therapeutic effect. The combination of a colloidal metal with such agents in a vector composition reduces toxicity while maintaining or increasing the therapeutic results thereby improving the efficacy as higher concentrations of agents may be administered, or by allowing the use of combinations of different agents. The use of colloidal metals in combination with agents in vector compositions therefore allows the use of higher than normal concentrations of agents or administration of agents that normally are unusable due to their toxicity, to be administered to humans or animals. Preferably, the vector compositions further comprise one or more types or sizes of PEG or derivatives of PEG.

One embodiment of the present invention comprises methods for using a vector composition comprising an agent associated with the colloidal metal as a vaccine preparation. Among the many advantages of such a vaccine is the reduction of toxicity of normally toxic agents. The vector compositions used as a vaccine against agents may be prepared by any method. For example, the vector composition of an admixture of agents and colloidal metal is preferably injected into an appropriate animal. For example, rabbits weighing between approximately two to five kilograms suffered no noticeable side-effects after they were administered, every two weeks, a composition comprising colloidal gold and the agent, 1 mg of cytokine, either IL-1 or IL-2. Because the agent is not toxic when administered according to the present invention, the optimal quantity of the agent, which can function as an antigen, can be administered to the animal. The vector compositions according to the present invention may be administered in a single dose or may be administered in multiple doses, spaced over a suitable time scale. Multiple doses are useful in developing a secondary immunization response. For example, antibody titers have been maintained by administering boosters once a month.

The vaccine compositions may further comprise a pharmaceutically acceptable adjuvant, including, but not limited to Freund's complete adjuvant, Freund's incomplete adjuvant, lipopolysaccharide, monophosphoryl lipid A, muramyl dipeptide, liposomes containing lipid A, alum, muramyl tripeptide-phosphatidylethanoloamine, keyhole limpet hemocyanin. A preferred adjuvant for animals is Freund's incomplete adjuvant and Alum for humans, which preferably is diluted 1:1 with the compositions comprising a colloidal metal and an active agent.

A preferred method of use of the compositions of the present invention comprises administering to a human or animal an effective amount of a vector composition comprising a colloidal metal admixed with at least one agent, wherein the composition when administered to a human or animal, is less or non-toxic, or has fewer or less severe side effects when compared to administration of the agent alone or in compositions without colloidal metals. The vector compositions according to the present invention can be administered as a vaccine against a normally toxic substance or can be a therapeutic agent wherein the toxicity of the normally toxic agent is reduced thereby allowing the administration of higher quantities of the agent over longer periods of time.

In practicing these embodiments, the route by which the composition is administered is not considered critical. The routes that the composition may be administered according to this invention include known routes of administration, including, but are not limited to, subcutaneous, intramuscular, intraperitoneal, oral, and intravenous routes. A preferred route of administration is intravenous. Another preferred route of administration is intramuscular.

For example, it is known that Interleukin-2 (IL-2) displays significant therapeutic results in the treatment of renal cancer. However, the toxic side effects of administration of IL-2 result in the death of a significant number of the patients. In contrast, if a vector composition comprising at least IL-2 and a colloidal metal is administered, little or no toxicity is observed and a strong immune response occurs in the recipient. The doses previously used for IL-2 therapy have been on the order of $21\times10^6$ units of IL-2 per 70 kg person per day ($7\times10^6$ units of IL-2 per 70 kg person TID). One unit equals approximately 50 picograms, 2 units equals approximately 0.1 nanograms, so $20\times10^6$ units equals 1 milligram. In one embodiment of this invention, the amount of IL-2 that has been given to rabbits is approximately 1 mg per 3 kg rabbit. In effect, the studies of the effects of the administration of agents described herein have included doses of more than 20 times higher than that previously given to humans.

In another embodiment, where IL-2 (1 mg per 3 kg animal) was administered to 3 rabbits every third day for a two-week period, all the animals appeared to be clinically sick, and two of the animals died from the apparent toxic effects of the IL-2. When the same dose of IL-2 was used in vector compositions comprising colloidal gold and then administered to three rabbits for the same two-week period, no toxicity was observed and a significant antibody response resulted in all three animals. A "positive antibody response" as used herein is defined as a three to fourfold increase in specific antibody reactivity, as determined by direct ELISA, comparing the post-immunization bleed with the preimmunization bleed. A direct ELISA is done by binding IL-2 onto a microtiter plate, and determining the quantity of IgG bound to the IL-2 on the plate, by goat anti-rabbit IgG conjugated to alkaline phosphatase. Therefore, it is thought that the biological effects of the IL-2 remain. As the toxicity effects have been minimized, larger concentrations of IL-2 may be administered if necessary where a larger, more effective immune response is required.

The present invention comprises methods for treating diseases by administering vector compositions comprising one or more agents and a colloidal metal. The vector compositions may further comprise PEG or derivatives of PEG. It is theorized that after administration, the agents are released from the colloidal metal. Though not wishing to be bound by any theory, it is thought that the release is not simply a function of the circulation time, but is controlled by equilibrium kinetics.

When a vector composition comprising at least a colloidal metal and at least one agent was incubated with cells for 25 days, it was found that only 5% of the agent was released from the colloidal metal. Thus, it is theorized that circulation time alone does not explain the mechanism through which the agents are released from the complex in vivo. However, it has been found that the amount of agent released is, in part, related to the concentration of the complex in the body. When various dilutions of compositions were analyzed (CytELISA™ assay system CytImmune Sciences, Inc.), it was found that the more dilute solutions of the complex released a significantly greater amount of agent. For example, there was essentially no release of agent in a 1:100 dilution of the complex, whereas over 35,000 pg. of the agent was released in a 1:100,000 dilution of the composition.

Therefore, the lower the concentration of the composition in the larger solution, the greater the amount of agent released. The higher the concentration of the composition, the lower the amount of agent released. Thus, it is theorized that due to the continuous in vivo dilution of the compositions by blood and extracellular fluids, it is possible to achieve the same therapeutic effect by administering a lower dose of an agent to a patient than can be administered by previously known methods.

It is also theorized that the amount of agent released from the compositions of the present invention is related to the amount of agent initially bound to the colloidal metal. More agent is released in vivo from vector compositions having a greater amount of agents initially bound. Thus, the skilled artisan could control the amount of agents delivered by varying the amount of agent initially bound to the colloidal metal.

These combined properties provide methods by which a large amount of agents can be bound to a colloidal metal, thereby rendering the agent less toxic than if administered alone. Then, a small amount of the vector composition can be administered to a patient resulting in the slow release of the agent from the complex. These methods provide an extended, low dose of the agents for the treatment of diseases such as cancer and immune diseases.

The compositions of the present invention are useful for the treatment of a number of diseases including, but not limited to, cancer, both solid tumors as well as blood-borne cancers, such as leukemia; autoimmune diseases, such as rheumatoid arthritis; hormone deficiency diseases, such as osteoporosis; hormone abnormalities due to hypersecretion, such as acromegaly; infectious diseases, such as septic shock; genetic diseases, such as enzyme deficiency diseases (e.g., inability to metabolize phenylalanine resulting in phenylketanuria); and immune deficiency diseases, such as AIDS.

Methods of the present invention comprise administration of the vector compositions in addition to currently used therapeutic treatment regimens. Preferred methods comprise administering vector compositions concurrently with administration of therapeutic agents for treatment of chronic and acute diseases, and particularly cancer treatment. For example, a vector composition comprising the agent, TNF, is administered prior to, during or after chemotherapeutic treatments with known anti-cancer agents such as antiangiogenic proteins such as endostatin and angiostatin, thalidomide, taxol, melphalan, paclitaxel, taxanes, vinblastin, vincristine, doxorubicin, acyclovir, cisplatin and tacrine. All currently known cancer treatment methods are contemplated in the methods of the present invention and the vector compositions may be administered at different times in the treatment schedule as necessary for effective treatment of the cancer.

A preferred method comprises treatment of drug-resistant tumors, cancer or neoplasms. These tumors are resistant to known anti-cancer drugs and therapeutics and even with increasing dosages of such agents, there is little or no effect on the size or growth of the tumor. Known in cancer treatment is the observation that exposure of such drug resistant tumor cells to TNF resensitizes these cells to the anti-cancer effect of these chemotherapeutics. Evidence has been published that indicates that TNF synergizes with topoisomerase II-targeted intercalative drugs such as doxorubicin to restore doxorubicin tumor cell death. Also interferon (IFN) is known to synergize with 5-fluorouracil to increase the chemotherapeutic activity of 5-fluorouracil. The present invention can be used to treat such drug-resistant tumors. A preferred method comprises administration of compositions comprising vectors having TNF and derivatized PEG bound to colloidal gold. With the pretreatment of a patient with a subclinical dose of TNF-cAu-PT, the tumor sequesters the TNF vector, sensitizing the cells to subsequent systemic chemotherapy. Such chemotherapies include, but is not limited to doxorubicin, other intercalative chemotherapies, taxol, 5-fluorouracil, mitaxantrone, VM-16, etoposide, VM-26, teniposide, and other non-intercalative chemotherapies. Alternatively, another preferred method comprises administration of compositions comprising vectors having TNF and at least one other agent effective for the treatment of cancer. For example, a PT-cAU$_{(TNF)}$ doxorubicin vector is administered to patients who have drug resistant tumors or cancer. The amount administered is dependent on the tumor or tumors to be treated and the condition of the patient. The vector composition allows for greater amounts of the chemotherapeutic agents to be administered and the vector also relieves the drug-resistant characteristic of the tumor.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Preparation of Colloidal Gold Sols

Colloidal gold is produced by the reduction of chloroauric acid ($Au^{+3}$; $HAuCl_4$), to neutral gold ($Au^0$) by agents such as sodium citrate. The method described by Horisberger, (1979) was adapted to produce 34 mm colloidal gold particles. This method provided a simple and scalable procedure for the production of colloidal gold. Briefly, a 4% gold chloride solution (23.03% stock; $dmc^2$, South Plainfield, N.J.) and a 1% sodium citrate solution (wt/wt; J.T. Baker Company; Paris, Ky.) were made in de-ionized $H_2O$) ($DIH_2O$). 3.75 ml of the gold chloride solution was added to 1.5 L of $DIH_2O$. The solution was vigorously stirred and brought to a rolling boil under reflux. The formation of 34 nm colloidal gold particles was initiated by the addition of 60 ml of sodium citrate. The solution was continuously boiled and stirred during the entire process of particle formation and growth as described below.

The addition of sodium citrate to the gold chloride initiated a series of reduction reactions characterized by changes in the color of the initial gold chloride solution. With the addition of the sodium citrate the color of the gold chloride solution changed from a golden yellow to an intermediate color of black/blue. The completion of the reaction was signaled by a final color change in the sol from blue/black to cherry red. After the final color change the solution was continuously stirred and boiled under reflux for an additional 45 minutes. Subsequently, the sol was cooled to room temperature and filter through a 0.22 u cellulose nitrate filter and stored at RT until use.

The formation of colloidal gold particles occurs in two stages: nucleation and particle growth. Particle nucleation was initiated by the reduction of $Au^{+3}$ to $Au^0$ by sodium citrate. This step is marked by a color change of the gold chloride solution from bright yellow to black. The continuous layering of free $Au^{+3}$ onto the $Au^0$ nuclei drives the second stage, particle growth. Particle size is inversely related to the amount of citrate added to the gold chloride solution: increasing the amount of sodium citrate to a fixed amount of gold chloride results in the formation of smaller particles, while reducing the amount of citrate added to the gold solution results in the formation of relatively larger particles.

Similar to the nucleation reaction, colloidal gold particle formation is also correlated with a change in the solution's color. However, unlike the initial reaction, this second color change is directly related to particle size. When small particles (i.e., 12-17 nm) are made the sol is orange to red in color; when medium sized particles (i.e., 20-40 nm) are made the sol appears red to burgundy in color and when large particles (i.e., 64-97 nm) are made the sols appear violet to brown in color. Critical to both particle nucleation and growth was the vigorous stirring of the reactants. Inadequate stirring at any step during the process resulted in the formation of heterogeneous particles with larger than predicted diameters.

TEM (transmission electron microscopy) and dual angle light scattering interrogation of the colloidal gold preparations revealed that the size of the particles in the colloidal gold preparations were very close to their theoretical size of 34 nm. The particles were homogenous in size with a mean particle diameter of 34-36 nm and a polydispersity measure averaging 0.11 (Table IV). In this state the colloidal gold particles stayed in suspension by their mutual electrostatic repulsion due to the negative charge present on each particle's surface. Exposing these naked particles to salt solutions (i.e., NaCl at a 1% v/v final concentration) caused them to aggregate and ultimately precipitate out of solution. This process was blocked or inhibited by binding proteins (e.g., TNF) or other agents to the particles' surface.

Example 2

Metal Sources

Experiments were performed to see if the source of the starting gold reactants for the formation of the colloid formation affected the colloidal gold compositions. Gold chloride was purchased from two different commercial sources: Degussa Metals Catalysts Cerdec ($dmc^2$) and Sigma Chemical Company. Both gold preparations were analyzed for the presence of contaminating metals as well as other substances. The results from these studies are listed in Table II. Although the gold concentrations in each preparation were within reported values, it is clear that the Sigma preparation contains higher levels of Mg, Ca and Fe.

TABLE II

Purity of gold chloride salts used to generate colloidal gold

| Element | $dmc^2$ | Sigma |
|---|---|---|
| Na | <25 ppm | >21 ppm |
| Mg | <25 ppm | >60 ppm |
| Ca | <25 ppm | >60 ppm |
| Fe | <25 ppm | >60 ppm |

TEM of the particles revealed further differences between the particles made with different gold chloride sources, from Sigma and from $dmc^2$. The colloidal gold sols were manufactured as described above and observed used TEM. After cooling, 10 ml of the sol was centrifuged to concentrate the particles. The resultant supernatant was removed by aspiration and the colloidal gold pellet was resuspended by gentle tituration. The pellet was prepared for transmission electron microscopy following standard procedures.

The particles made with the Sigma gold chloride are translucent with apparent striations. The striations have been reported to be due to the presence of trace contaminants, such as those identified above. In contrast, the particles made with $dmc^2$ gold chloride are electron dense with very few striations.

Example 3

Generation of Colloidal Gold Sols Using Sigma and $dmc^2$ Gold Chloride

The above data suggested that the gold chloride from $dmc^2$ contained lower levels of contaminating elements. To determine the effect of these two qualitatively different sources of gold chloride, colloidal gold sols were generated using the two different sources of the salt. The procedure for creating the colloidal gold particles follows the procedure originally described by Horisberger, and in Example 1. Briefly, a 4% gold chloride (in water) solution was made from the $dmc^2$ and Sigma stock preparations. 3.75 ml of each solution was added to individual flasks each containing 1.5 L of water. The solution was brought to a rolling boil, kept boiling under reflux, and vigorously stirred. 22.5 ml of a 1% sodium citrate solution was added to each flask. The solutions in both flasks were kept boiling until the well-described process of colloidal gold formation was complete, signaled by a color conversion from gold to black to cherry red. Once the sols turned a cherry red, they were allowed to boil under reflux, with constant stirring, for an additional 45 min. After cooling, the sols were filtered through a 0.22 μm nitrocellulose filter and stored at room temperature until use.

A qualitative comparison of the two sols was made with a standard laboratory spectrophotometer, running a UV/VIS wavelength scan. The results revealed that the two batches of sols contained colloidal gold particles with a similar mean diameter, as indicated by the wavelength where the sol exhibits the greatest absorbance. However the most striking difference between the two preparations is that the sol made with the $dmc^2$ material had 3-times the number of particles as those made with the Sigma material. In addition, it appeared that the distribution around the lambda max is wider in the Sigma preparation than for the $dmc^2$ preparation, indicating that the particles generated with the Sigma salt are more heterogeneous than those generated with the $dmc^2$ gold chloride.

Example 4

Analytical Comparison of the Colloidal Gold Sols

The above qualitative differences were confirmed by quantitative particle characterization with a Brookhaven Particle Sizer. For these studies the samples of particles from each gold source were prepared according to manufacture's instruction. The data are presented below in Tables II and III. The data confirmed that the particles in both preparations are of approximately the same size (34-37 nm). Nevertheless the sols made with the $dmc^2$ material have a 3-fold higher particle density than those made with the Sigma material. In addition, the particles made with the Sigma gold chloride preparation are 2.5 times more heterogeneous (i.e., have a larger value for their polydispersity) than the particles made with the $dmc^2$ material (Table IV).

TABLE III

Variable wavelength analysis of colloidal gold sols generated with $dmc^2$ and Sigma gold chloride

| Sample | λ Max | Absorbance | λ@ ½ Max |
|---|---|---|---|
| $dmc^2$ | 526 nm | 2.8899 | 576 |
| Sigma | 529 nm | 1.0513 | 587 |

TABLE IV

Mean particle size and distribution of colloidal gold sols generated with $dmc^2$ and Sigma gold chloride

| | Particle Size | Mean Polydispersity |
|---|---|---|
| $dmc^2$ | 34.0 | 0.096 |
| Sigma | 36.9 | 0.230 |

Example 5

Determination of the pH Binding Optimum

The binding of proteins to colloidal gold is known to be dependent on the pH of the colloid gold and protein solutions. The pH binding optimum of TNF to colloidal gold sols was empirically determined. This pH optimum was defined as the pH that allowed TNF to bind to the colloidal gold particle, but blocked salt-induced (by NaCl) precipitation of the particles. Naked colloidal gold particles are kept in suspension by their mutual electrostatic repulsion generated by a net negative charge on their surface. The cations present in a salt solution cause the negatively charged colloidal gold particles, which normally repel each other, to draw together. This aggregation/precipitation is marked by a visual change in the color of the colloidal gold solution from red to purple (as the particles draw together) and ultimately black, when the particles form large aggregates that ultimately fall out of solution. The binding of proteins or other stabilizing agents to the particles' surface will block this salt-induced precipitation of the colloidal gold particles.

The pH optimum of TNF binding to colloidal gold was determined using 2 ml aliquots of 34 nm colloidal gold sol whose pH was adjusted from pH 5 to 11 (determined by using pH strips) with 1N NaOH. TNF (Knoll Pharmaceuticals; purified to homogeneity) was reconstituted in $diH_2O$ to a concentration of 1 mg/ml and further diluted to 100 μg/ml in 3 mM TRIS base. To determine the pH binding optimum for TNF, 100 μl of the 100 μg/ml TNF stock was added to the various aliquots of pH-adjusted colloidal gold. The TNF was incubated with the colloid for 15 minutes. Subsequently 100 μl of a 10% NaCl solution was added to each of the aliquots to induce particle precipitation. The optimal binding pH was defined as the pH, which allowed TNF to bind to the colloidal gold particles, while preventing the particles' precipitation by salt.

Example 6

Saturation Binding Studies

Based on the data obtained from the pH binding study, the pH of 34 nm colloidal gold sol was adjusted to pH 8 with 1 N NaOH. The sol was divided into 1 ml aliquots to which increasing amounts (0.5 to 4 μg of TNF) of a 100 μg of TNF/ml solution were added. After binding for 15 minutes the samples were centrifuged at 7,500 rpm for 15 minutes. A 10 μl sample of the supernatant was added to 990 μl of EIA assay diluent (provided as part of a commercial EIA kit for TNF measurement; Cytlmmune Sciences, Inc., College Park, Md.). The remainder of the supernatant was removed by aspiration and the colloidal gold pellet was resuspended to its original volume in a PEG 1450/$diH_2O$ solution pH 8. 10 μl of the resuspended pellet was added to 990 μl of EIA assay diluent. The reconstituted pellet and supernatant solutions were serially diluted and analyzed for TNF concentration by a quantitative commercial EIA (Cytlmmune Sciences, Inc, College Park, Md.).

Figure 2:
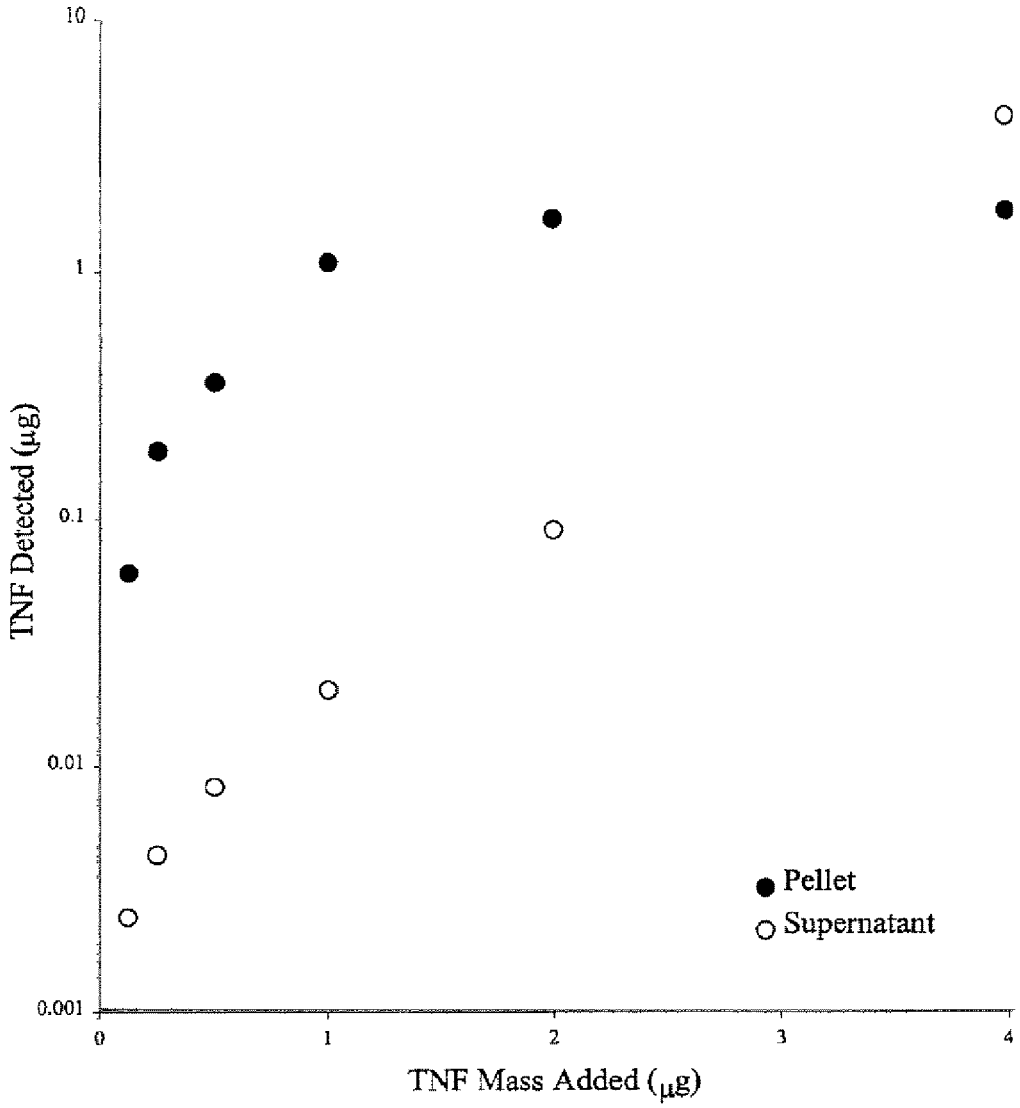
FIG. 2 is graph showing saturation binding of TNF to colloidal gold.

Using the data from the pH binding study, the pH of 50 ml of colloidal gold was adjusted between 8.0-9.0. At this pH the binding of TNF to a fixed volume of colloidal gold exhibited saturation kinetics (FIG. 2). As shown in FIG. 2, at 0.5 μg of TNF/ml of gold sol virtually all the TNF was bound to the colloidal gold particles with an insignificant amount (2-5%) present as free TNF in the supernatant. This colloidal gold-TNF complex precipitated in the presence of salt, indicating that this concentration of TNF did not fully coat the colloidal gold particles and is a sub-saturating dose of TNF. By increasing the TNF concentration the amount of TNF bound to the colloidal gold particles progressively increased with relatively little change in the amount of free TNF measured in the supernatant. This increase in particle-bound TNF paralleled the increase in the particles' stability against salt-induced precipitation. Saturation of the colloidal gold particles with TNF occurred when all the binding sites on the surface of the particles were bound with TNF. Saturation of the colloidal gold particles occurred at a binding concentration of 4 μg/ml (FIG. 2). Binding at doses above 4 μg/ml resulted in increasing amounts of free TNF measured in the supernatant.

In FIG. 2, saturation binding of TNF to colloidal gold is shown. 50 ml of 34 nm colloidal gold sol was pH adjusted to 8 using 1 NaOH, and then divided into 1 ml aliquots. Increasing volumes of a stock TNF (100 μg/ml in 3 mM TRIS) solution were added to the aliquots and allowed to bind for 15 minutes. The samples were centrifuged at 7500 rpms for 15 minutes. A 10 μl sample of the supernatant was diluted in a Tris buffered saline milk solution (assay diluent). The remainder of the supernatant was removed by aspiration and the colloidal gold pellet was resuspended by gentle tituration. 10 μl of the resuspended pellet was diluted in assay diluent. Both pellet and supernatant samples were serially diluted and measured for TNF concentration by EIA (CytImmune Sciennces, Inc.).

Example 7

Large Scale Production of the Various Colloidal Gold Vectors

The in vivo assessment of the colloidal gold-TNF particles, also referred to as vectors, required the scaling-up of all manufacturing procedures. Large (8 L) batches of colloidal gold were manufactured as described above. The manufacturing procedure of the colloidal gold sols was adapted to 8 L colloidal gold production. A reflux apparatus (Kontes Glass, Vineland, N.J.) was used to generate 8 L of colloidal gold for in vivo experiments. Briefly, 8 L of $diH_2O$ was heated to a rolling boil. 20 ml of gold chloride was added through one port, followed by the addition of 320 ml of sodium citrate. The color change of the resultant sol was the same as that seen in the smaller preparation. Once the cherry red color was achieved the sol was allowed to cool overnight, and was then sterile filtered as described above.

The particles made using large scale amounts were essentially the same as particles made using bench scale methods. See Table V.

TABLE V

Characterization of bench scale and large scale preparations of 34 nm colloidal gold sols by dynamic light scattering.

| Preparation | Measured Size nm | Polydispersity |
|---|---|---|
| Bench Scale/1.5 L | 36 | 0.131 |
| Large Scale/(8.0 L) | 34 | 0.096 |

Next, the uniform coating of the colloid particles had to be accomplished. This was an important consideration since analysis demonstrated that the binding between the colloidal gold particles and the TNF molecules was nearly instantaneous. Consequently, simply adding a concentrated protein solution to a large volume of gold would result in particles that were differentially coated with TNF. To optimize the interaction of the particles and TNF molecules, apparatus that allowed complete interaction between the colloidal gold sol and the TNF solution was used. A schematic representation of the apparatus is shown in FIG. 1. The apparatus reduced the mixing volume between the naked colloidal gold particles and TNF by drawing each component into a small mixing chamber (a T-connector). The colloidal gold particles and the TNF solutions were physically drawn into the T-connector by a single peristaltic pump that drew the colloidal gold particles and the TNF protein from two large reservoirs. To further ensure proper mixing, an in-line mixer (Cole-Palmer Instrument Co., Vernon Hills, Ill.) was placed immediately downstream of the T-connector. The mixer vigorously mixed the colloidal gold particles with TNF, both of which were flowing through the connector at a flow rate of approximately 1 L/min.

Prior to mixing, the pH of the gold sol was adjusted to pH 8 using 1 N NaOH, while the recombinant human TNF was reconstituted and prepared in 3 mM Tris. The solutions were added to their respective sterile reservoirs using a sterile closed tubing system. Equal volumes of the colloidal gold sol and the TNF solution were added to the appropriate reservoirs. Since the gold and TNF solutions were mixed in equal volumes, the initial starting TNF concentration for each test vector was double the final concentration. For example, to make 4 L of a 0.5 μg/ml solution of cAu-TNF, 2 L of colloidal gold were placed in the gold reservoir, while 2 L of a 1 μg/ml TNF solution was added to the TNF container.

Once the solutions were properly loaded into their reservoirs, the peristaltic pump was activated, drawing the TNF and the colloidal gold solutions into the T-connector, through the in-line mixer, the peristaltic pump, and into a large collection flask. The resultant mixture was stirred in the collection flask for 15 minutes. After this binding step, 1 ml samples from each of the formulations were collected and tested for salt precipitation. A 1.0 μg/ml and a 4.0 μg/ml preparations were processed as described below, while a third solution, a second 0.5 μg/ml preparation, was treated by adding niPEG-thiol 5,000 (10% v/v addition of a 150 μg/ml stock in $diH_2O$) at a final concentration of 15 μg/ml. This third solution, a PEG-thiol-colloidal gold-TNF (PT-cAu-TNF) solution, was incubated for an additional 15 minutes. Two other PT-cAu-TNF formulations were made using a 20,000 and a 30,000 MW form of PEG-Thiol. During these studies additional controls were tested for comparison including PEG-Thiol/naked colloidal gold or the 4 μg/ml cAu-TNF vector.

Colloidal gold bound TNF in each preparation was separated from free TNF by diafiltration through a 50,000 MWCO BIOMAX diafiltration cartridge (Millipore Corporation, Chicago, Ill.). An aliquot of the permeate (i.e., free TNF) was removed and set aside for TNF determination. For mass balance determination, the total volume of the permeate was measured. The retentate, which contained the TNF bound colloidal gold, was sterile filtered through a 0.22 micron filter and a 10 μl aliquot was taken for TNF analysis. The remainder of the retentate was frozen at −80° C. for storage. Subsequent to the determination of the TNF concentrations, a solution of native TNF was manufactured in 3 mM Tris and used as the control for the in vivo studies.

Example 8

Initial Formulation of the Colloidal Gold TNF Vector

This series of experiments was designed to determine the effect of various TNF:colloidal gold binding ratios on the in vivo biologic activity of the colloidal gold TNF vector. Three different formulations of the colloidal gold TNF vector were made based on the data generated from the TNF-binding-to-colloidal-gold saturation curve. The three vectors were generated by binding TNF at 1, 2 or 4 μg of TNF/ml of colloidal gold solution. These three vectors differed in their ability to remain colloidal following the addition of salt. The 1 μg/ml vector precipitated immediately (i.e., the color of the colloidal changed from cherry red to black) upon the addition of the salt solution. In contrast the color of the 2 μg/ml vector turned from red to purple, indicating an aggregation of the colloidal gold particles. Finally, the 4 μg/ml preparation remained red after the addition of salt, indicating that the particles remained colloidal and did not interact. Although the colloidal nature of the particles in the 1 and 2 μg/ml vectors was altered by their exposure to salt, they remained stable when incubated with normal human plasma. These data suggested that plasma factors, most likely blood borne proteins, bound to the particle and immediately stabilized it against precipitation. Thus exposing these vectors to blood prevented their precipitation and allowed for their investigation in vivo.

Comparative safety studies of the three cAu-TNF vectors and native TNF were done in MC-38 tumor-burdened C57/BL6 mice. The toxicity profile of native TNF was dose-dependent. 5 μg of native TNF/mouse caused piloerection and diarrhea within 1-2 hours of injection. With increasing doses of native TNF more severe toxicities were observed. At a dose of 15 μg of TNF/mouse, 50% of the animals became hypothermic and unresponsive, and ultimately died within 24 hours. The mice were scored at different times after injection using the following toxicity rating scale: 0=normal activity; 1=piloerection; 2=loose stools; 3=lethargy; 4=unresponsive; and 5=death.

Figure 3:
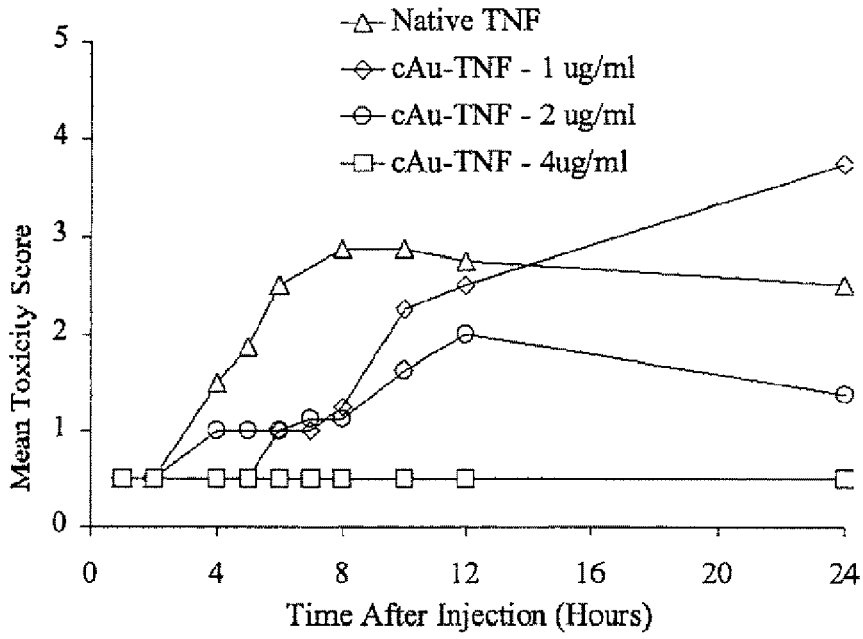
FIG. 3A is a graph showing the effect of TNF:gold binding ratios on the safety of the cAu-TNF vector.
FIG. 3B is a graph showing the effects of a TNF:gold binding ratios on the safety of the cAu-TNF vector.
FIG. 3C is a chart showing the anti-tumor efficacy a cAu-TNF and native TNF.
FIG. 3D is a chart showing TNF distribution profiles after 1 hour.
FIG. 3E is a chart showing TNF distribution profiles after 8 hours.
FIG. 3F is a graph of pharmacokinetic profiles of native TNF and a cAu-TNF vector in MC38 tumor-burdened C57/BL6 mice.
Figure 3:
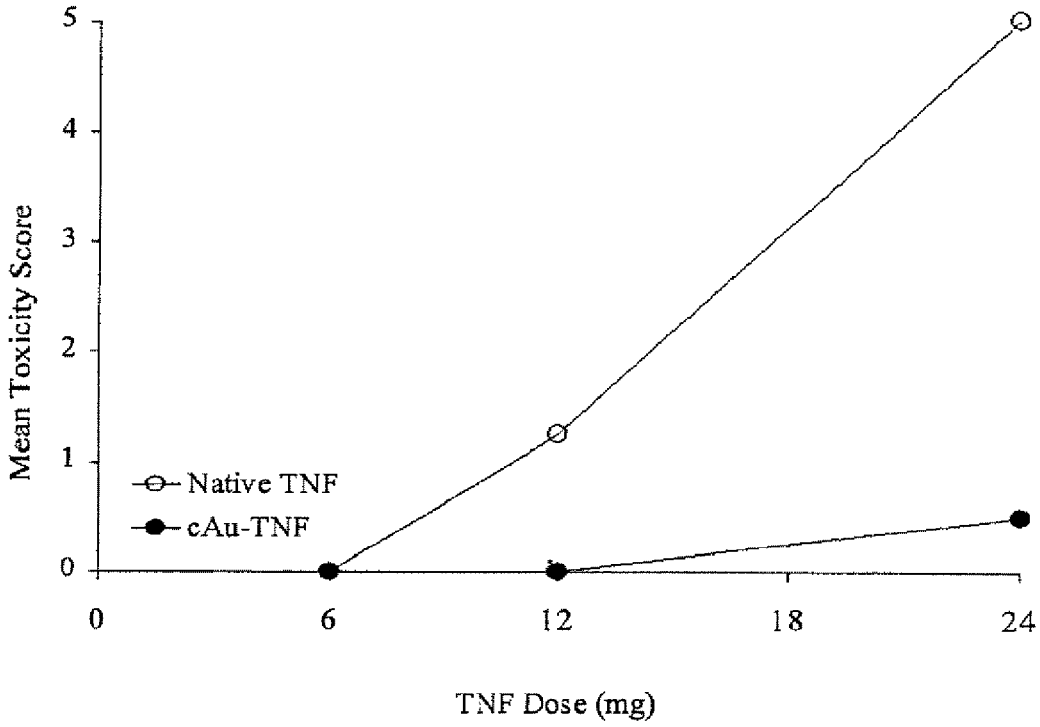
Figure 3:
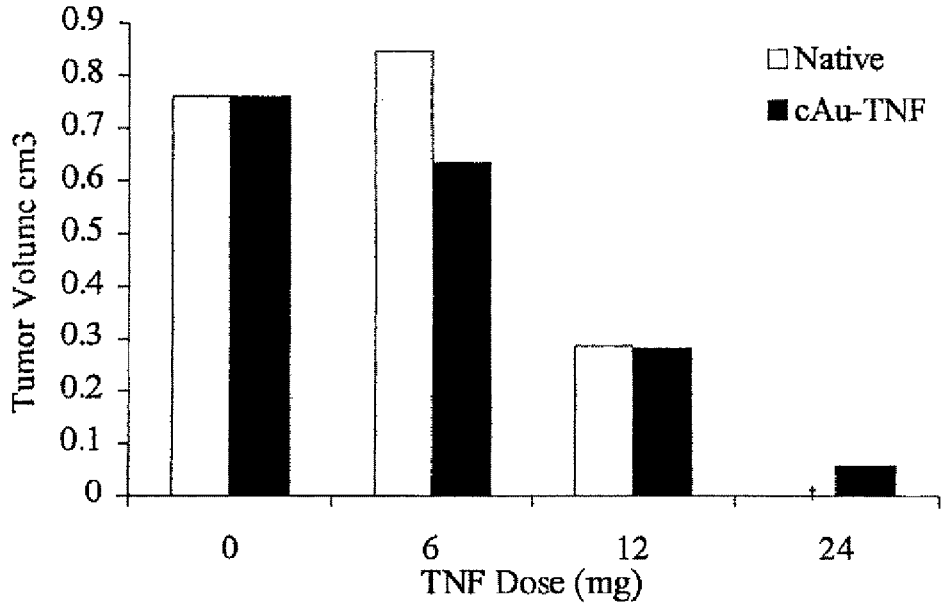
Figure 3:
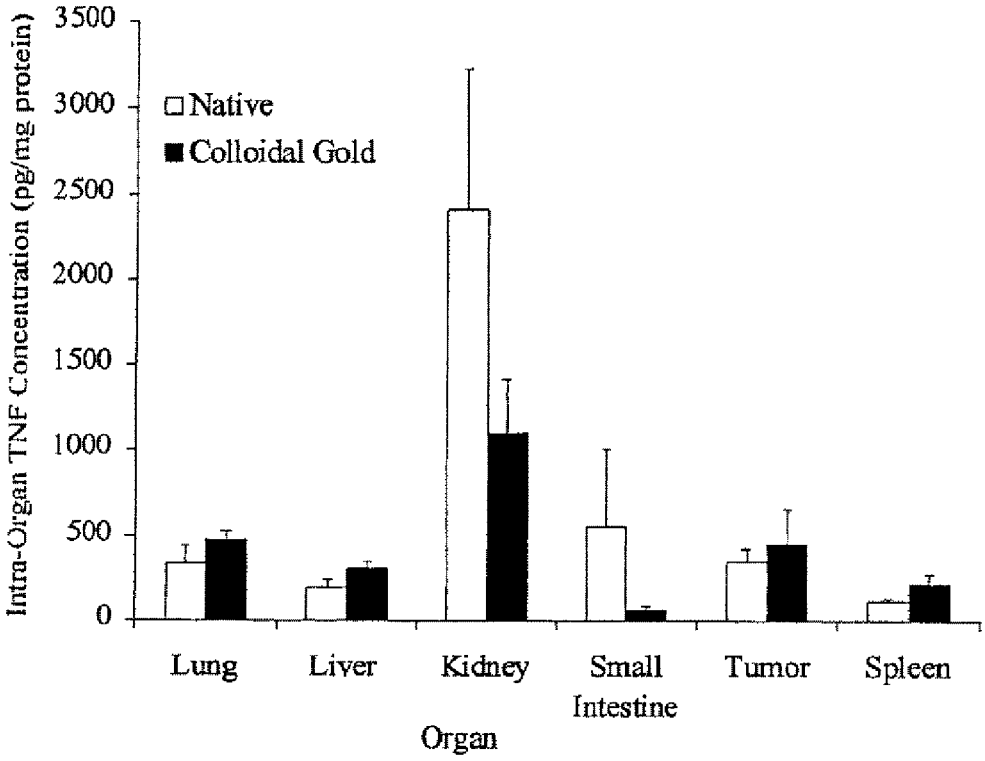
Figure 3:
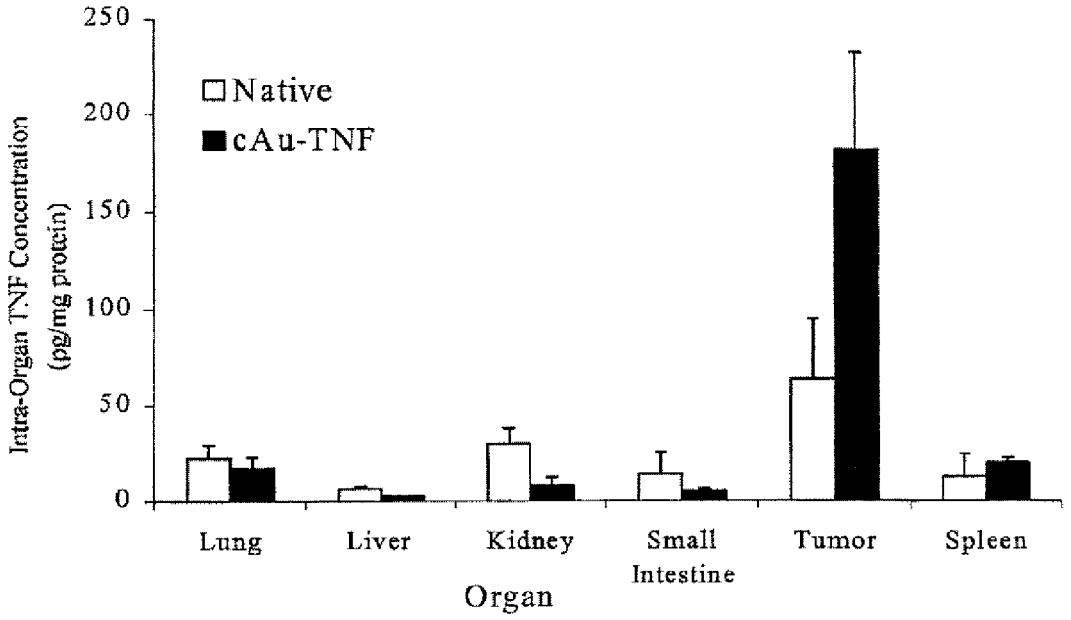
Figure 3:
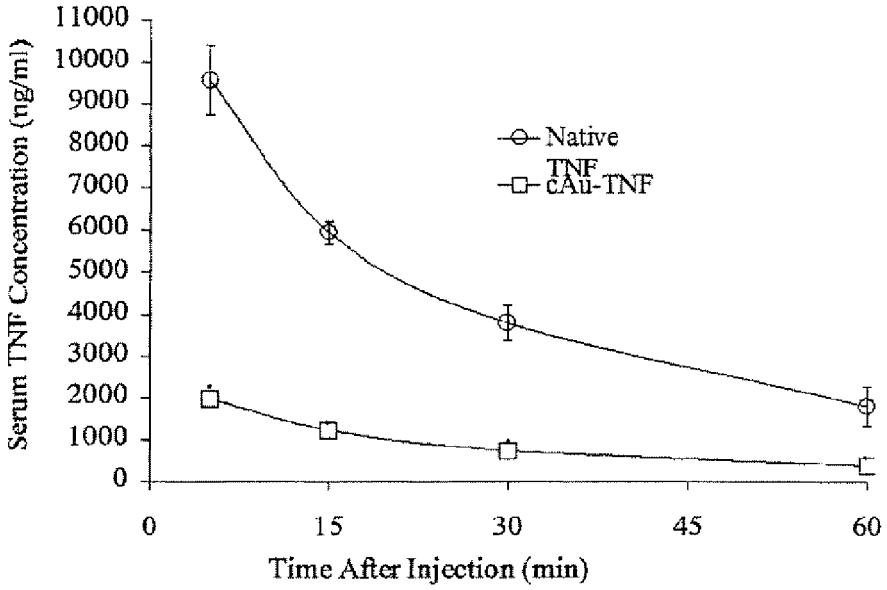

Although these three cAu-TNF vectors were biologically similar to native TNF preparations in the in vitro bioassay, their toxicity profiles were quite different in the C57/BL6-MC-38 tumor model. Increasing the initial binding concentration of TNF from 1.0 to 4.0 μg/ml increased the relative safety of the cAu-TNF vector (FIG. 3A). Mice injected with 15 μg of native TNF had a 50% mortality rate. A 15 μg injection of the 1.0 μg/ml cAu-TNF vector also caused a 50% mortality rate. In contrast, mice receiving 15 μg of the cAu-TNF bound at 2.0 μg/ml had a reduced mortality rate of 25%. Finally, none of the mice injected with 15 μg of the 4.0 μg/ml cAu-TNF preparation died. This last group of animals exhibited only transient toxicities that resolved within 8 hours of treatment.

FIG. 3A shows the effect of TNF:gold binding ratios on the safety of the cAu-TNF vector. Three different colloidal gold TNF vectors were generated based on their relative degree of TNF saturation of the colloidal gold particles. MC-38 tumor burdened C57/BL6 mice (n=4/group) were intravenously injected with 15 μg of either native TNF, not bound to a gold vector, or one of the three cAu-TNF vectors. The mice were scored at various points after the injection using the toxicity rating scale described. The percent survival for the treatments were: Native TNF=50%, 1 μg/ml cAu-TNF vector=25%, 2 μg/ml cAu-TNF vector=75% and 4 μg/ml cAu-TNF vector=100%.

A second dose escalation and safety study with the 4.0 μg/ml cAu-TNF vector indicated that this composition was safer on a dose-to-dose basis when compared to native TNF (FIG. 3B). Treatment with 12 μg or 24 μg of this cAu-TNF vector per mouse resulted in significant tumor reduction (FIG. 3C). In effect, this cAu-TNF vector increased the relative safety of any given dose of TNF and at a maximally tolerated dose improved the treatment's efficacy. These safety and efficacy data suggested that this cAu-TNF vector effectively increased the therapeutic index for TNF, since the drug's efficacy was maintained while its safety was improved.

FIG. 3B shows the dose escalation and toxicity of native TNF and 4 μg/ml cAu-TNF in MC-38 tumor-burdened C57/BL6 mice. MC-38-tumored C57/BL6 mice (n=4/group/dose) were intravenously injected with increasing doses of native TNF or the 4 ug/ml cAu-TNF vector. Mice were scored using the toxicity rating scale described. The percent of the animals surviving native TNF treatment at 6, 12, and 24 μg/mouse were 100%, 75% and 0% respectively. All animals receiving the cAu-TNF treatment survived. *$p \leqq 0.05$.

FIG. 3C shows a comparison of the anti-tumor efficacy of native TNF and the 4 μg/ml cAu-TNF vector in MC-38 tumor-burdened C57/BL6 mice. The anti-tumor responses for the various treatment groups described in FIG. 3B were measured by determining three dimensional (L×W×H) tumor measurements 10 days after treatment. Data are presented as the mean±SEM of tumor volume (in $cm^3$) for the various groups. All animals receiving the 24 μg native TNF treatment died within 24 hours of treatment.* $p \leqq 0.05$ versus untreated controls.

These data strongly suggested a preferred composition for the cAu-TNF vector, which was then tested for its biodistribution. Over time, the biodistribution of TNF was different between those animals treated with native TNF and those treated with cAu-TNF. One hour after injection, mice receiving native TNF had higher levels of TNF in the kidney compared to cAu-TNF treated mice (FIG. 3D). In contrast, eight hours after injection, mice receiving the colloidal gold formulation had higher levels of TNF in the tumor (FIG. 3E). Thus it seemed that the cAu-TNF vector was improving safety and maintaining efficacy by targeting the delivery of TNF to the tumor.

FIGS. 3D and 3E show the comparison of the TNF distribution profiles in MC-38 tumor burdened C57/BL6 mice intravenously injected with 15 μg native TNF or the 4 μg/ml cAu-TNF vector. MC-38 tumor-burdened C57/BL6 mice (n=4/group/treatment/time point) were intravenously injected with 15 μg of native TNF or the 4 μg/ml cAu-TNF vector. A group of animals were sacrificed either 1 (FIG. 3D) or 8 hours (FIG. 3E) after injection and organs were collected. The organs were flash frozen at −80° C. and stored until analyzed. The organs were quickly defrosted by addition 1 ml of PBS (containing 1 mg/ml of bacitracin and PMSF) and homogenized using a polytron tissue disrupter. The homogenate was centrifuged at 5000 rpms and the resultant supernatant was analyzed for TNF concentration and total protein as described above. Data are presented as the mean ±SEM from four organs per time point.

Autopsy of the animals revealed a potential problem with this cAu-TNF vector. The dramatic black color of the liver and the spleen of cAu-TNF vector treated mice argued that part of the improved safety may have been due to the vector's uptake and clearance by these organs. Further studies revealed that this uptake was rapid, often occurring within 5 minutes after intravenous injection. Visual inspection of these organs suggested that the black color of these organs was not different from the black precipitates formed when naked colloidal gold particles were exposed to salt. Also, it is unlikely that the black color of these organs was due to trapped blood in these organs since the animals were heparinized and extensively perfused prior to organ collection. These data suggested that a majority of the vector was rapidly cleared by the components of the RES, leading to the conclusion that the cAu-TNF vector was not optimized.

Additional evidence supporting this hypothesis was derived from pharmacokinetic studies that compared TNF levels between native TNF and two cAu-TNF vectors. Contrary to expectations, administration of the 4 ug/ml cAu-TNF vector resulted in lower initial serum levels than native TNF (FIG. 3F). The TNF levels of those mice given the cAu-TNF vector were consistently 2-5 fold lower than that measured in animals receiving native TNF. This difference in PK was more pronounced with a 0.5 μg/ml cAu-TNF vector, where the serum levels of TNF were nearly 10-fold lower than that seen with the native preparation. Mice receiving cAu-TNF vectors, regardless of the formulation (i.e., 0.5 or 4.0 μg/ml), consistently exhibited lower blood levels of TNF than mice receiving the native protein. Taken together, the vector biodistribution and PK data argued that uptake by the RES needed to be significantly reduced or eliminated for this vector to effectively target the tumor.

FIG. 3F shows a comparison of the pharmacokinetic profiles of native TNF or the 4 ug/ml cAu-TNF vector in MC38-tumor burdened C57/BL6 mice. MC-38 tumor burdened mice (n=3/group/time point) were intravenously injected with 10 μg of either native TNF or the 4 ug/ml cAu-TNF vector. At the indicated time points the mice were anesthetized and bled through the retro-orbital sinus. The blood samples were allowed to clot and were centrifuged at 14,000 rmps. The resultant sera samples were analyzed for TNF concentration using a commercial EIA for TNF. Data are presented as the mean±SEM serum concentration from three mice per time point. *$p<0.05$.

Example 9

Vectors to Avoid Clearance by the RES and Target the Delivery of TNF to Solid Tumors Recognition and clearance of foreign objects by the RES has been seen with other drug carriers. For liposomes and biodegradable polymers this problem was addressed by surface modifications using a variety of PEG stabilizers as well as block co-polymers, such as polaxamer and polaxamine. Numerous stabilizers, including those used in liposome formulations (e.g., carbowax 20M, tetronic 407, pluronic 908) were added to the 4.0 ug/ml cAu-TNF vector. None of the reagents effectively blocked the vector's uptake by the RES.

Next, the amount of TNF bound per particle was reduced. TNF was first bound to the colloidal gold particles at a sub-saturating dose (i.e., 0.5 μg/ml). Thiol-derivatized polyethylene glycol (PEG-Thiol; MW=5,000) was then added to the particles. This small, linear PEG-Thiol reagent was chosen because thiol groups could bind directly to the particle's surface, presumably in between the molecules of TNF. This new vector was tested in the MC-38 tumor burdened C57/BL6 mice.

This composition of the colloidal gold bound TNF vector was formulated by binding TNF and an additional agent to the same particle of colloidal gold. This vector was formed by first binding TNF to colloidal gold at a sub saturating dose of 0.5 μg/ml. A derivatized PEG was then added to the vector. The derivatized PEG was a thiol-derivatized polyethlylene glycol (methoxy PEG-Thiol, MW: 5000 dalton, PEG-Thiol, Shearwater Corp., Huntsville, Ala.). The final concentration of PEG-Thiol was 15 μg/ml, which was added as a 10× concentrate in $diH_2O$. Thiol-derivatized PEGs are good components for colloidal gold vectors since the thiol group binds directly to the surface of the colloidal gold particles. A 5,000 MW thiol-PEG was the first thiol-derivatized PEG to be tested. Additionally, efficacy experiments using mPEG-thiol with MWs of 20,000 and 30,000 daltons were performed as described below.

The biodistribution profile seen following the administration of the PEG-Thiol modified cAu-TNF (PT-cAu-TNF) vector was different from those observed with the previous cAu-TNF vectors. With this new vector, the liver and spleen did not visibly take up the PT-cAu-TNF vector, (FIG. 4A) as occurred with the 0.5 and 4.0 μg/ml cAu-TNF vectors (FIG. 4B). FIG. 4C shows an untreated liver and spleen. As striking as the inhibition of the RES uptake, was the apparent accumulation of the PT-cAu-TNF vector in the MC-38 tumor, since the tumors acquired the bright red/purple color of the colloidal gold particle within 30-60 minutes of vector's administration. The sequestration continued throughout the time course of the study and was coincident with the accumulation of TNF in the tumor and extended blood residence time of TNF.

Unlike the black color of the gold that accumulated in the liver and spleen following the 0.5 μg/ml and 4.0 μg/ml cAu-TNF vector treatment, the color of the gold observed accumulating in the tumor following the administration of the PT-cAu-TNF was reddish-purple. This difference is significant because it indicates that the gold particles remained in a colloidal state during their residence in the circulation and their accumulation in the tumor. Interestingly, the pattern of PT-cAu-TNF accumulation in and around the tumor site changed with time. The PT-cAu-TNF was initially (i.e., 0-2 hours) sequestered solely in the tumor. With time, vector staining was apparent on the skin and on the surrounding ventral tissues of the mouse. During the blunt dissection of sacrificed animal's tumor, it was observed that the extra-tumor staining in these animals was restricted to the dermal layer where the tumor cells were initially implanted. Minimal staining was present on the underlying muscle bed on which the tumor rested. This observation suggested that the peripheral staining may be due to the accumulation of the vector in the blood vessels, possibly new blood vessels, feeding the tumor mass. Currently, it is unknown whether the staining represents an active sequestration of the drug in these blood vessels or the passive accumulation due to tumor saturation with the vector.

To determine whether the staining reflected a hemorrhagic response cause by TNF, the staining pattern mice receiving a 15 μg injection of the 4 ug/ml cAu-TNF vector or native TNF was compared with those receiving the same dose of the PT-cAu-TNF vector. Mice treated with the 4 ug/ml cAu-TNF vector began to exhibit the tumor scar formation which typically follows intravenous administration of TNF. A similar pattern of scarring was observed following native TNF treatment. The pattern of the scar staining observed with the native TNF or the 4 ug/ml cAu-TNF vector treatments was clearly distinct from the pattern of staining observed following PT-cAu-TNF vector treatment. Further evidence that the staining pattern observed following the administration of the PT-cAu-TNF vector was obtained from mice receiving PEG-Thiol colloidal gold particles initially bound with murine serum albumin (MSA). The PT-cAu-MSA vector caused staining of the tumor like that of the PT-cAu-TNF vector albeit at a much slower rate. The staining of the tumor was similar in color to that observed with PT-cAu-TNF treatment. However the change in tumor coloration was only evident after 4 hours of treatment, compared with the 30-60 minute color change observed with the PT-cAu-TNF vector. Furthermore, the intensity of the staining was lower than that observed with the PT-cAu-TNF vector.

Figure 4:
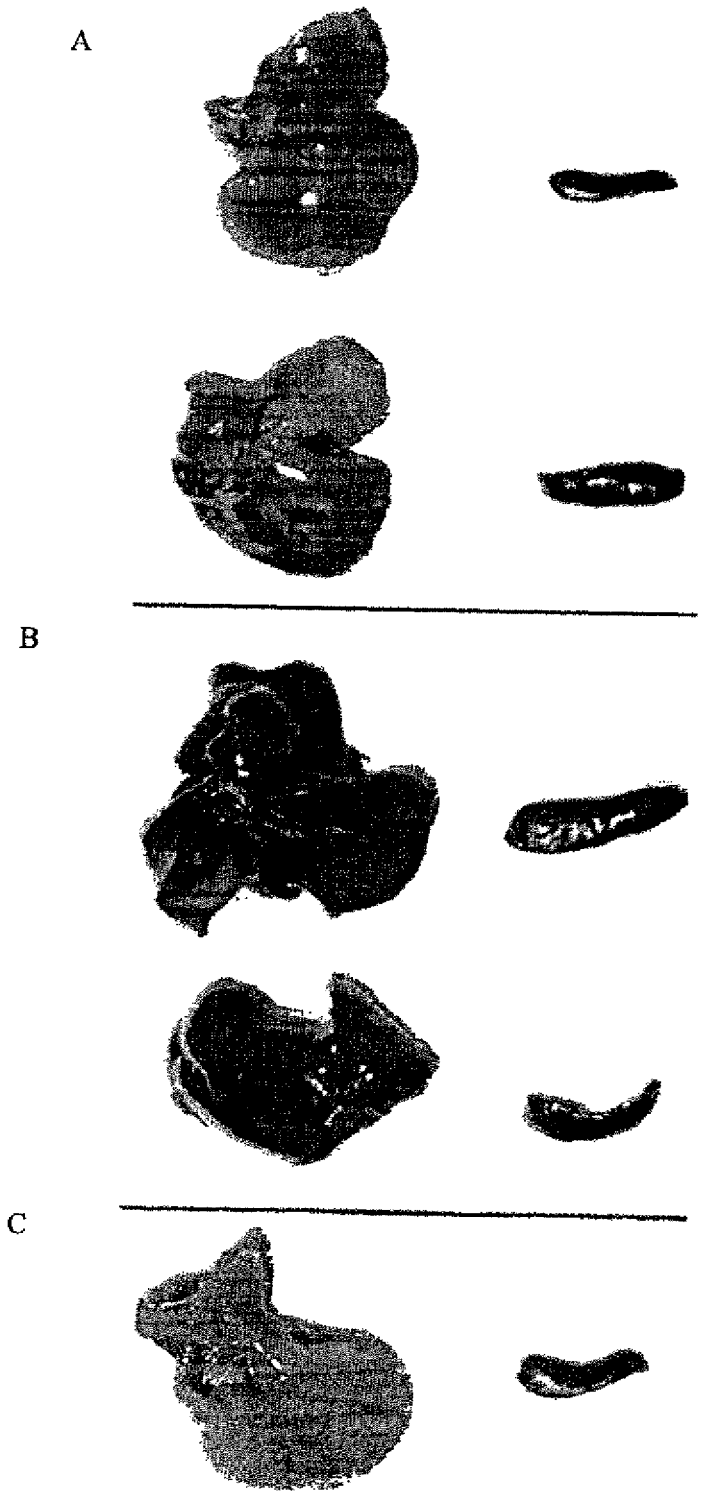
FIG. 4, A-C, shows liver and spleen of mice treated with PT-cAu-TNF vectors, (A), cAU-TNF vectors, and no treatment (C).

FIG. 4 shows inhibition of the RES-mediated uptake of the colloidal gold TNF vector by PEG-Thiol vectors. The PT-cAu-TNF vector was developed using specified ratios of TNF and PEG-Thiol as described. After binding, the vector was concentrated by diafiltration and analyzed for TNF concentration by EIA. 15 μg of the PT-cAu-TNF vector was intravenously injected into MC-38 tumor-burdened C57/BL6 mice. The mice were sacrificed 5 hours after the injection and perfused with heparinized saline. The livers (on left of picture) and spleens were photographed.

Example 10

Pharmacokinetic and Distribution Analyses

In general, these experiments comprise native TNF, cAu-TNF (4 μg/ml), or PT-cAu-TNF, (0.5 μg/ml) vectors that were generated as described above. Depending on the study, 5-20 μg of native or one of the cAu-TNF vectors were intravenously injected, through the tail vein, of MC-38 tumor-burdened mice. Mice were bled at 5, 180, and 360 minutes after injection through the retro-orbital sinus. The blood was allowed to clot and the resultant serum was collected and frozen at −20° C. for batch TNF analysis by EIA (Cytlmmune Sciences, Inc.). At selected time points, various organs were collected and flash frozen. To determine TNF content, the organs were defrosted, homogenized, and centrifuged at 14,000 rpms for 15 minutes. The supernatant was analyzed for TNF concentration as described above, as well as for total protein by determining the sample's absorbance a 280 nm. Organ TNF concentrations were normalized to total protein.

A. Gold Distribution

Various organs, including liver, lung, spleen, brain, and blood, were examined for the presence of elemental gold following the intravenous injection of 15 μg of the PEG-Thiol stabilized 0.5 μg/ml cAu-TNF vector. The mice were sacrifice 6 hours the injection; blood was collected and the various organs harvested, including liver, spleen, and tumor. After removal, the organs were digested in aqua-regia (3 parts concentrated HCl to 1 part concentrated nitric acid) to extract the gold present in these organs. The extraction was carried out over 24 hours, after which, the samples were centrifuged at 3500 rpms for 30 minutes. The supernatants were analyzed for the presence of total organ gold concentration by inductively coupled plasma spectroscopy. The results are reported as total organ gold concentration (in ppm) in FIG. 5A. The results demonstrate that the intra-tumor concentration of gold was nearly 2-fold higher than that measured in liver and nearly 7-fold higher than that found in the spleen. Although this pattern suggests that the vector was retained in the tumor compared to other organs, we observed that the highest level of gold was still in the circulation of these animals.

Figure 5:
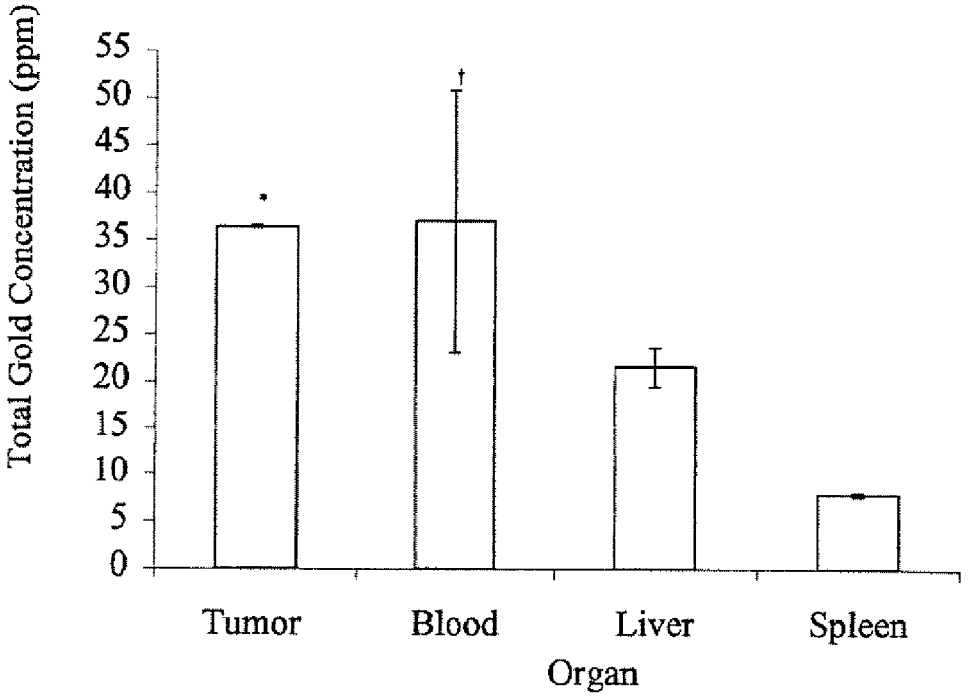
FIG. 5A is a graph showing gold distribution in various organs.
FIG. 5B is a graph showing TNF pharmacokinetic analysis.
FIG. 5C is a graph showing the intra-tumor TNF distribution over time.
FIG. 5D is a chart comparing the intra-tumor TNF concentrations with different vectors.
FIGS. 5E and F are graphs showing the distribution of TNF in various organs over time.
Figure 5:
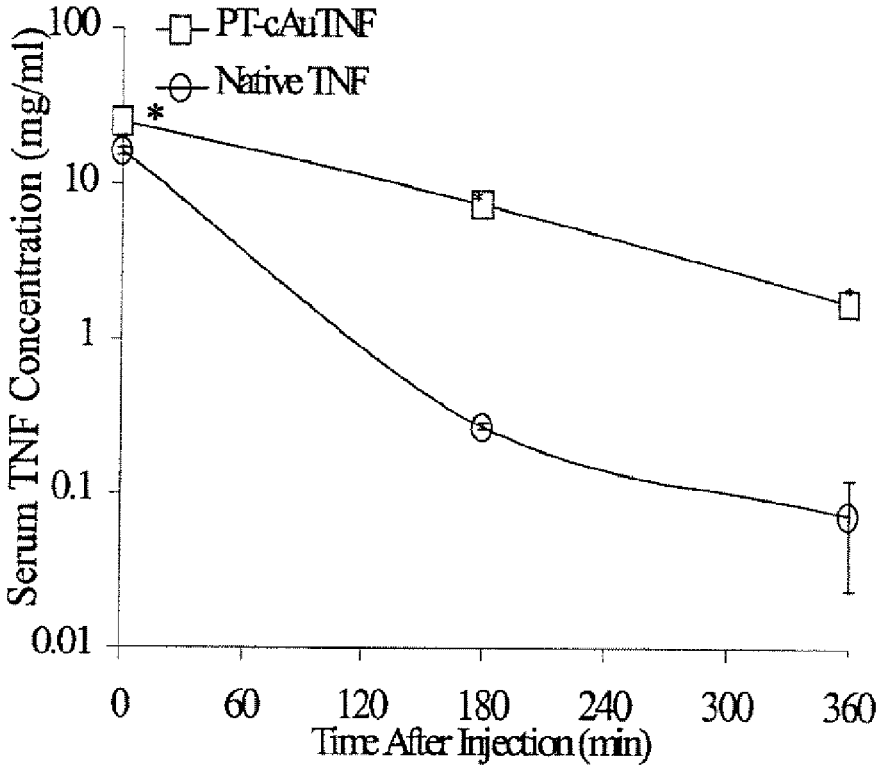
Figure 5:
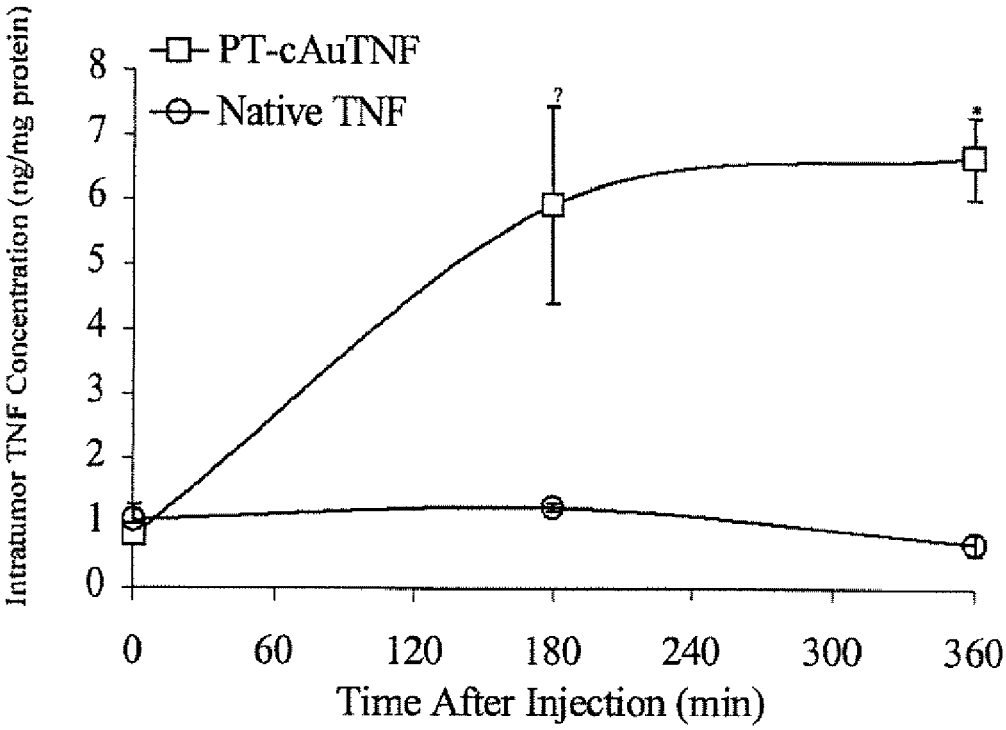
Figure 5:
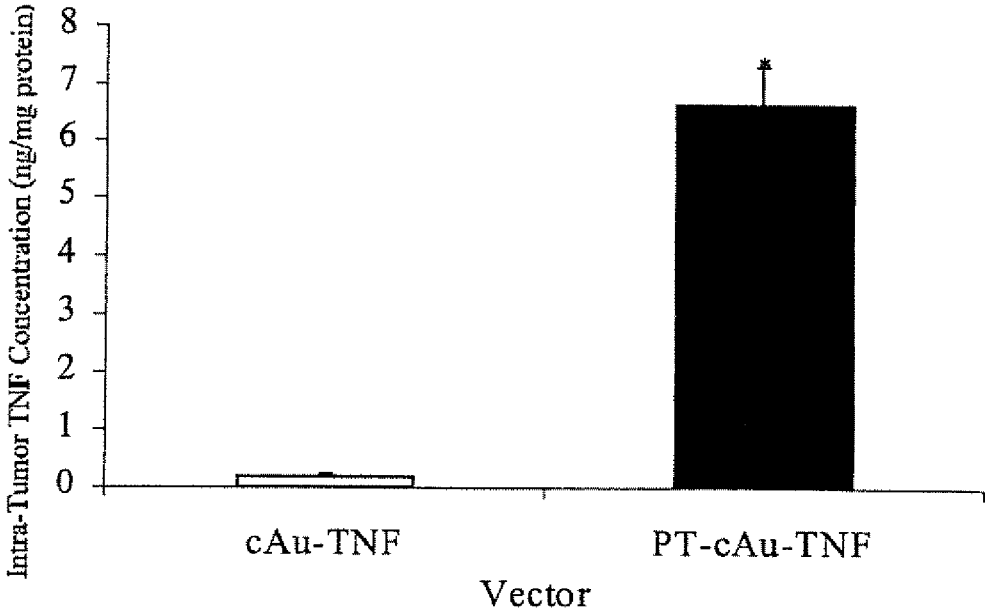
Figure 5:
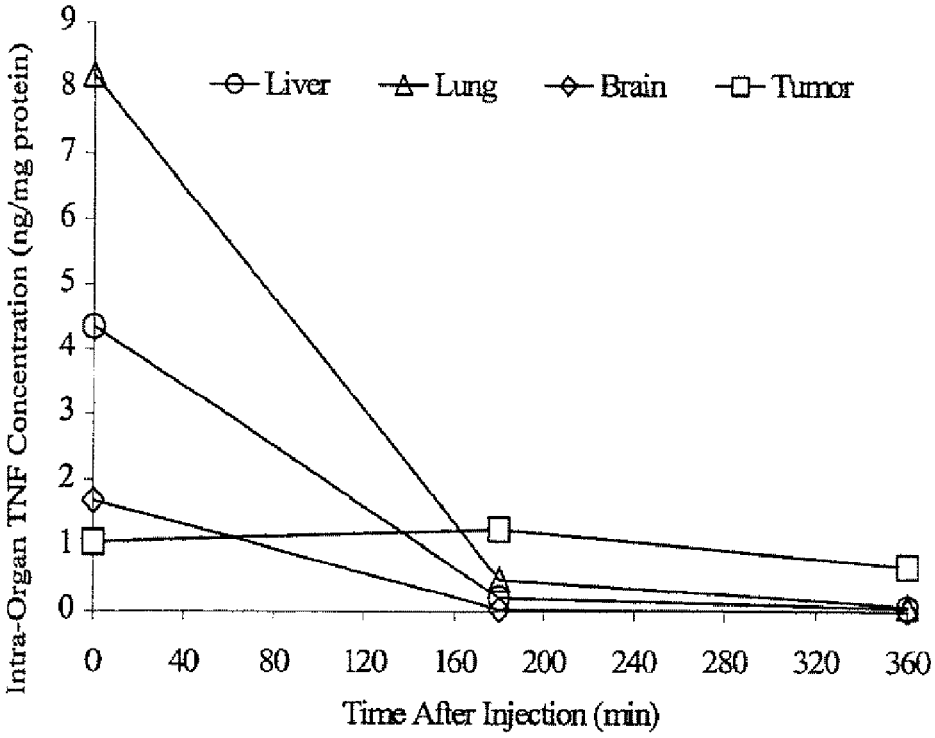
Figure 5:
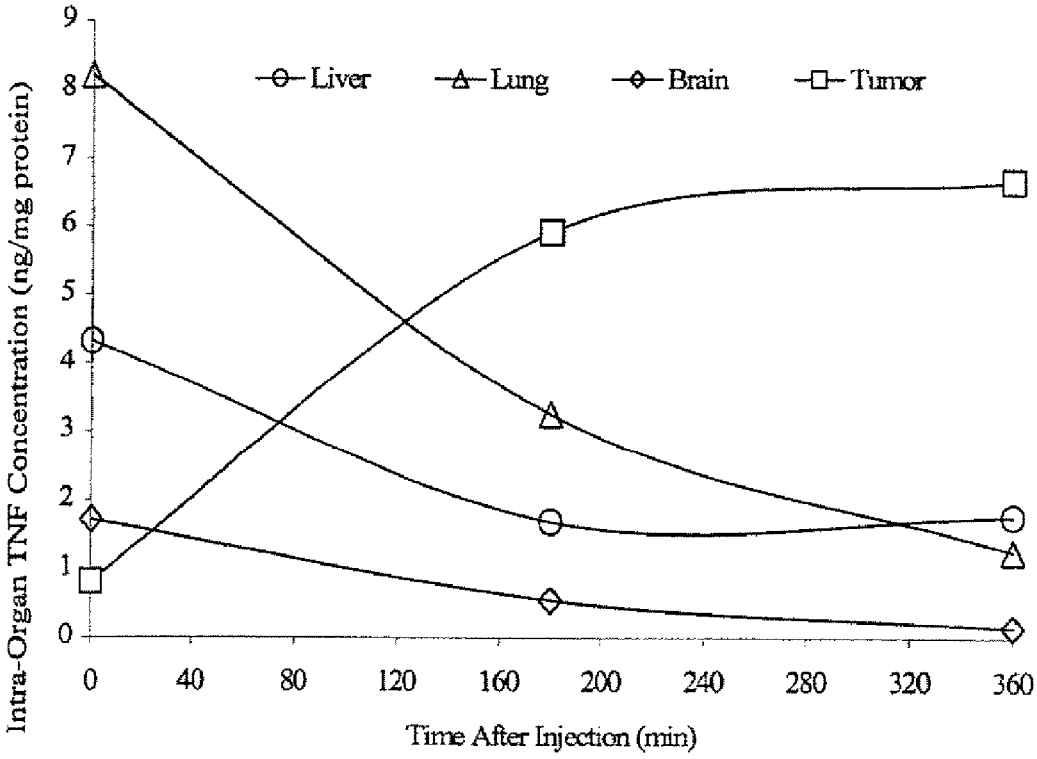

In FIG. 5A, gold distribution in various organs of MC-38 tumor burdened C57/BL6 mice is shown. The supernatants were analyzed for the presence of total organ gold concentration by inductively coupled plasma spectroscopy. The results are reported as total organ gold concentration (in ppm) for 3 mice per organ. *p<.0.05 versus liver and spleen; \ p<0.05 versus spleen.

B. Distribution and Pharmacokinetics of TNF

The sequestration of colloidal gold within the tumor mass was paralleled by the prolonged presence of the drug vector in the circulation as well as the active accumulation of TNF in the tumor. Unlike the cAu-TNF vectors without derivatized PEG, injection of the PT-cAu-TNF vector resulted in elevated levels of TNF in the circulation throughout the time course studied. Six hours after injection with native TNF, the TNF levels were only 2% of that seen at 5 minutes (FIG. 5B). In contrast, mice receiving the PT-cAu-TNF vector had TNF blood levels which were approximately 30% of their maximal 5-minute values. At this 6-hour time point, blood TNF levels in mice treated with the PT-cAu-TNF formulation were 23-fold higher than those in mice treated with native TNF.

FIG. 5B shows the TNF pharmacokinetic analysis. Mice were bled through the retro-orbital sinus at 5, 180 and 360 minutes after the injection. The blood samples were centrifuged at 14,000 rpms and the resultant serum analyzed for TNF concentration using an EIA. Data are presented as the mean±SEM serum TNF concentration from 3 mice/time point. (*p<0.05).

In those animals treated with PT-cAu-TNF vector, TNF accumulated in the tumor. As shown in FIG. 5C, the maximal intra-tumor concentration of TNF observed in those mice treated with native TNF was 0.8 ng of TNF/mg protein. The peak amount was seen within five minutes of administration of the native TNF, and did not increase over the 6-hours. In contrast, those animals treated with PT-cAu-TNF vector had intra-tumor levels of TNF that increased over time. TNF was actively sequestered in the tumor of those animals treated with PT-cAu-TNF vector. By the end of the time period, nearly 10-times more TNF was found in the tumors of those animals treated with the PT-cAu-TNF vector compared to those treated with native TNF or the 4 μg/ml cAu-TNF vector (FIG. 5D).

In FIG. 5C, the intra-tumor TNF distribution over time is shown. Mice were sacrificed 5, 180 and 360 minutes after the injection of 15 μg of native TNF or PT-cAu-TNF vector. The tumors were removed and analyzed for TNF and total protein. Data are presented as the mean±SEM of tumor TNF concentration, expressed in ng TNF/mg of total protein, from 3 mice/time point/treatment group. (Δp<0.1, *p<0.05).

FIG. 5D shows a comparison of the intra-tumor TNF concentrations from animals injected intravenously with 15 μg of either the 4 μg/ml cAu-TNF vector or the PT-cAu-TNF vector.

The accumulation of the PT-cAu-TNF vector in the MC-38 tumor mass was not a passive event or just a function of the vector's extended residency time in the circulation since, over the same period of time, TNF did not accumulate in other organs, such as the lung, liver, and brain. Rather, the presence of TNF in these organs was similar in pattern to that seen in blood. Furthermore, the distribution of the drug in these non-targeted organs was similar to that seen with native TNF. Consequently, the accumulation of TNF resulting from the administration of the PT-cAu-TNF vector is specific to the tumor (FIGS. 5E and F).

FIGS. 5E and F show the distribution of TNF in various organs from MC-38 tumor-burdened C57/BL6 mice receiving either native TNF (FIG. 5E) or PT-cAu-TNF (FIG. 5F). Livers, lung and brains from the animals treated in this Example were processed and analyzed for TNF and protein concentrations. Data are presented as the mean±SEM of intra-organ TNF concentration from 3 mice/time point/formulation injected.

Example 11

Dose Escalation, Toxicity and Efficacy

Figure 6:
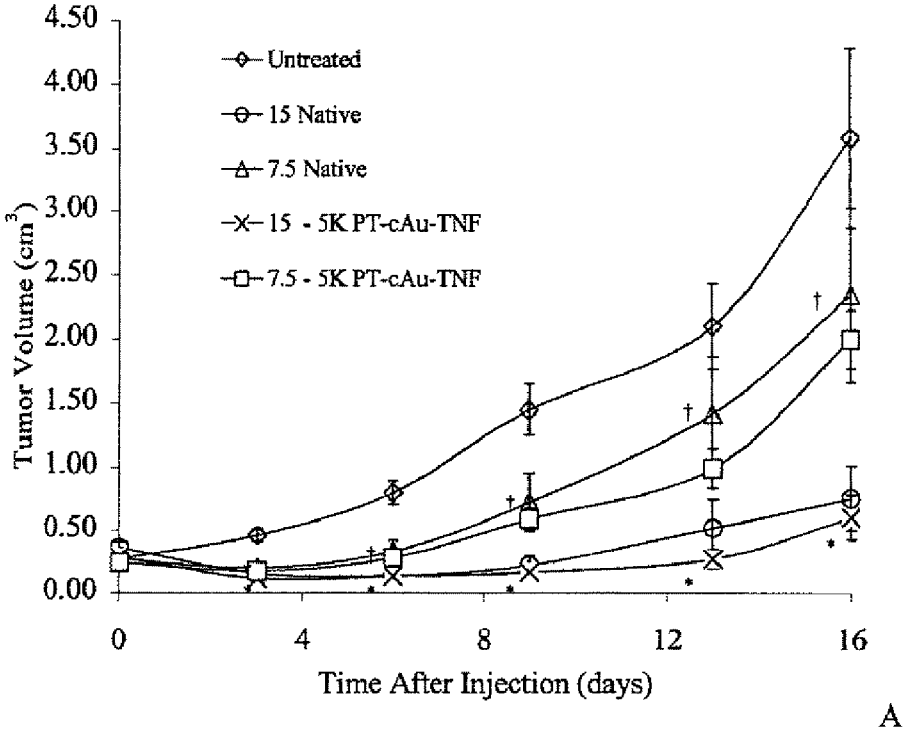
FIG. 6A is a graph comparing safety and efficacy of native TNF or PT-cAu-TNF vectors.
FIG. 6B is a graph comparing Native TNF and 20K-PT-cAU-TNF safety and efficacy.
FIG. 6C is a graph comparing Native TNF and 30K-PT-cAU-TNF safety and efficacy.
Figure 6:
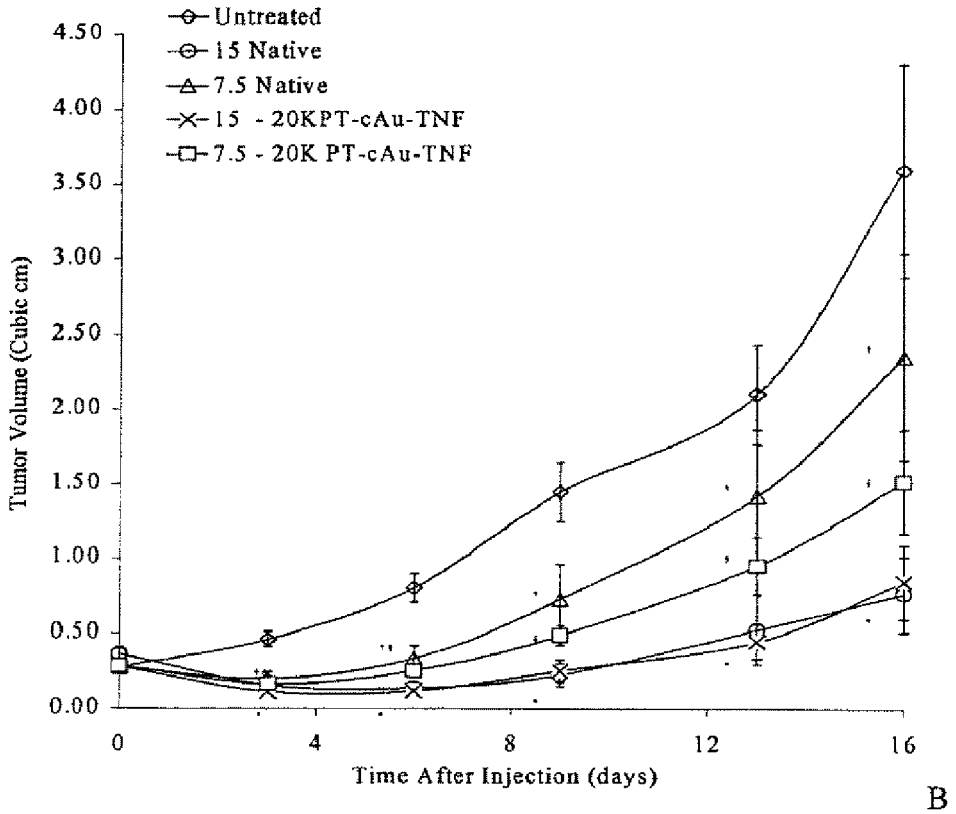
Figure 6:
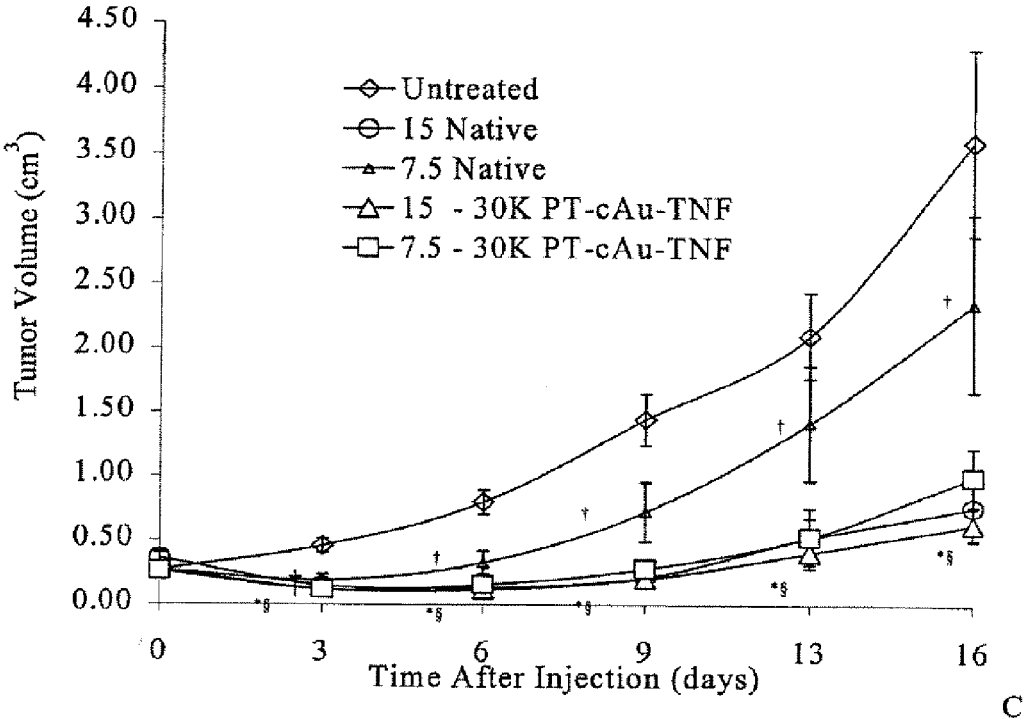

C57/BL6 mice were implanted with the colon carcinoma cell line, MC-38, as a model to compare the safety and efficacy of native and colloidal gold bound TNF preparations. C57/BL6 mice were implanted with $10^5$ MC-38 tumor cells in one site on the ventral surface. The cells were allowed to grow until they formed a tumor measuring 0.5 cm as determined by measuring the tumor in three dimensions (L×W×H). MC-38 tumor burdened C57/BL6 mice (n=4-9/group) were intravenously injected with increasing doses of native TNF, cAu-TNF vector, or PT-cAu-TNF vector. The mice were divided into nine groups with 4-9 animals/group. One group served as an untreated control group. Two groups were intravenously injected with either 7.5 or 15 μg of native TNF, (FIG. 6A). Two groups were intravenously injected with either 7.5 or 15 μg of a 20K-PT-cAu-TNF vector (FIG. 6B). Two groups were intravenously injected with either 7.5 or 15 μg of the 30K-PT-cAu-TNF vector (FIG. 6C). Tumor measurements were made on various days after the treatment on animals that survived TNF treatment. Statistical difference between the various groups was determined using a paired t-test.

The mice were scored at different times after injection using the following toxicity rating scale: 0=normal activity; 1=piloerection; 2=loose stools; 3=lethargy; 4=unresponsive; and 5=death. Animals scoring a 4 on two consecutive scoring times were sacrificed. Treatment efficacy was determined by monitoring the reduction in tumor volume induced by the various TNF treatments. The measures were compared to the initial tumor volume of each animal in the various groups as well as animals receiving saline injections (untreated controls). Untreated controls were sacrificed when their tumor volumes were 4 $cm^3$.

A 5K-PT-cAu-TNF vector, comprising PEG-thiol of 5,000 mw, was tested for safety and efficacy in dose escalation studies in MC-38 tumor-burdened mice. Like the 4 ug/ml cAu-TNF vector, the 5K-PT-cAu-TNF vector had an improved safety profile when compared to native TNF. At a dose of 15 μg of native TNF/mouse, 33% (3 out of 9) of the animals died within 24 hours of treatment. In addition, 7.5 μg of native TNF resulted in 1 out of the 9 animals dying. In contrast, none of the animals receiving either 7.5 or 15 μg of TNF bound to the 5K-PT-cAu-TNF vector died. These vector-treated animals exhibited only transient adverse clinical effects. No appreciable difference in the anti-tumor efficacy of the 5K PT-cAu-TNF vector, compared to native TNF, was observed following a single treatment (FIG. 6A). These findings were replicated in two experiments.

FIG. 6A is a graph comparing safety and efficacy of native TNF or PT-cAu-TNF vectors. \ $p<0.05$ for the 7.5 μg of dose of native TNF or PT-cAu-TNF treatment versus untreated controls. *$p<0.05$ for the 15 μg of dose of native or PT-cAu-TNF treatment versus untreated controls and 7.5 μg of dose native and PT-cAu-TNF.

The effect of PEG-thiol chain length on vector anti-tumor efficacy is shown in FIGS. 6B-C. At the highest TNF dose (15 μg) no differences were noted among any of the TNF vectors compared to native TNF. However, at a lower dose of 7.5 μg of TNF, a pattern emerged. As noted above, 5K PEG-thiol did not markedly improve the anti-tumor effect of the colloidal gold vector compared to native TNF. By increasing the PEG chain length to 20K there was a slight, non-statistical improvement in tumor reduction (FIG. 6B), while increasing it to 30K resulted in a marked, statistically significant improvement in tumor regression (FIG. 6C). With the 30K PT-cAu-TNF vector, animals treated with a dose of 7.5 μg of TNF via this vector, had residual tumors of similar size to those treated with 15 μg native TNF. In contrast to those treated with 15 μg of native TNF, the 30K PT-cAu-TNF-treated animals administered 7.5 μg of TNF experience no toxicity. In effect, a single injection of a 30K PT-cAu-TNF vector which gave less TNF but induced the same maximal anti-tumor regression as that seen with twice as much native TNF, and the treated subject survived the treatment. In this tumor model, a single injection of either 5K or 20K PEG-Thiol-cAu-TNF vector was safer than native TNF, and the 30K PEG-Thiol-cAu-TNF vector was both safer and more efficacious than the native molecule.

FIG. 6B is a graph comparing native TNF and 20K-PT-cAU-TNF safety and efficacy. †,§ $p<0.05$ for the 7.5 μg of dose of native TNF or PT-cAu-TNF vector treatment, respectively, versus untreated controls. 7.5 μg of the 20 K-PT-cAu-TNF vector was not statistically different form the 7.5 μg native group *$p<0.05$ for the 15 μg of dose of native or PT-cAu-TNF treatment versus untreated controls and the 7.5 μg of native and 20K-PT-cAu-TNF vector.

FIG. 6C is a graph comparing native TNF and 30K-PT-cAU-TNF safety and efficacy. \ $p<0.05$ for the 7.5 μg of dose of native TNF versus untreated controls. § $p<0.05$ for the 7.5 μg of dose of the 30K-PT-cAu-TNF vector treatment versus untreated controls and native TNF groups. *$p<0.05$ for the 15 μg of dose of native or PT-cAu-TNF vector treatment versus untreated controls and the 7.5 μg of dose native TNF. 7.5 μg of the 30K-PT-cAu-TNF was not statistically different from 15 μg of native or 30K-PT-cAu-TNF.

Example 12

Oral Administration of Colloidal Gold Compositions

The effect of the route of administration on the tumor sequestration of PT-cAu-TNF vectors was tested. The vector preparation is as described in previous Examples. Briefly colloidal gold is bound to TNF at a concentration of 0.5 μg/ml using the in-line mixing apparatus described above. Following a 15-minute incubation, 30,000 MW PEG-thiol (dissolved in pH 8 water) is added to the mixture at a final concentration of 12.5 μg/ml. The solution is stirred and immediately processed by diafiltration. The retentate is sterile filtered and aliquoted for storage at −40° C.

MC38 tumor-burdened C57/BL/6 mice were used as a model to determine the ability of orally administered PT-cAu-TNF vector to target the delivery of TNF and gold to the tumor site. For these studies mice (n=3) were anesthetized with 1 mg of pentobarbitol. After the animals were completely sedated, 26 μg of TNF bound onto the PT-cAu-TNF vector was administered through an oral cannula. The animals were allowed to recover and were allowed free access to food and water. The following day, it was observed that the tumors were the familiar red/blue color of the colloidal gold vector. These data show oral administration of the PT-cAu-TNF vector can be used to treat tumors.

Example 13

In Vitro Activity of Colloidal Gold Bound TNF Vectors

The in vitro activity of native TNF and the cAu-TNF vectors were determined by the WEHI-164 TNF bioassay as described by Khabar, K. S., Siddiqui, S., and Armstrong, J. A., WEHI-13 VAR: a stable and sensitive variant of WEHI 164 clone 13 fibrosarcoma for tumor necrosis factor bioassay, Immunol. Lett 46: 107-110 (1995). In this bioassay, $10^4$ WEHI-164 cells were plated in 12-well tissue culture clusters. The cells were cultured in DMEM supplemented with 10% FBS. Native TNF and four different cAU-TNF vectors prepared at 0.5, 1, 2 and 4 ug of TNF/ml of colloidal gold were incubated for 7 days with the cells at final TNF concentrations ranging from 1 mg/ml to 0.0001 mg/ml. Cell number was determined on day 7 using a Coulter Counter. Data are presented as the mean±SEM of the cell number for triplicate wells/TNF formulation.

The cAu-TNF vectors were biologically equivalent on a molar basis to native TNF in the WEHI 164 bioassay. For example, 12.5 ng of native TNF inhibited WEHI 164 cell growth by 50%, whereas the same 12.5 ng dose of the 1.0, 2.0 and 4.0 μg/ml cAu-TNF preparations inhibited WEHI 164 cell growth by 47%, 55%, and 52%, respectively.

Example 14

PEG-Thiol Vector for Tumor-targeted Delivery of Antiangiogenic Drugs

Figure 7:
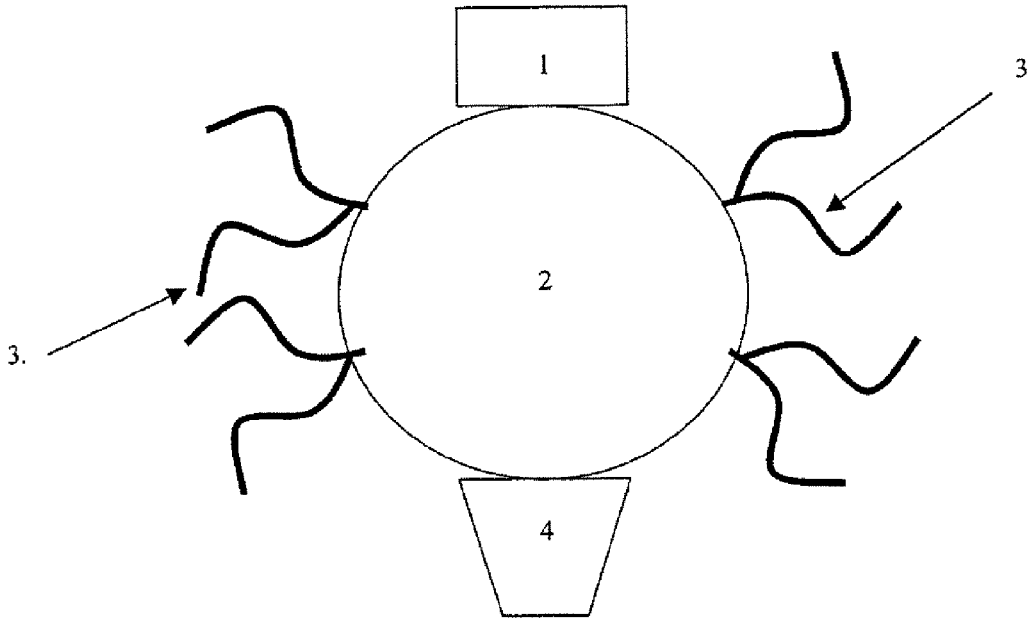
FIG. 7 is a schematic of a vector having multiple agents.

These experiments used a PT-cAU-TNF-endostatin vector, a vector comprising two agents. It is thought that the TNF provided targeting functions for delivery of the therapeutic agent, endostatin (END), to the tumor. It is also theorized that once at the target, both agents may provide therapeutic effects. An aspect of the vector composition is the ratio of the targeting molecule, the therapeutic molecule and the PEG. All three entities are found on the same particle of colloidal gold. A schematic of this vector is shown in FIG. 7. In FIG. 7, 1=an agent, such as an END molecule; 2=a colloidal gold particle; 3=derivatized PEG; and 4=a different agent or targeting molecule, such as a TNF molecule.

The PT-cAu$_{(TNF)}$-END vector, comprising derivatized PEG, TNF and endostatin (END) associated with a colloidal gold particle, was made using the apparatus described in FIG. 1. The PT-cAu$_{(TNF)}$-END was made in three steps. First, TNF associated with the gold particles at a very low subsaturating mass of TNF. Unlike the PT-cAu-TNF vector, which was made with a concentration of TNF of 0.5 μg/ml, this vector was made with a TNF concentration of 0.05 μg/ml. TNF (diluted in 3 mM CAPS buffer, pH=10) which was added to the reagent bottle of the apparatus at a concentration of 0.1 μg/ml. The second bottle in the apparatus was filled with an equal volume of colloidal gold at a pH of 10. TNF was bound to the colloidal gold particles by activation of the peristaltic pump as previously described. The colloidal gold-TNF solution was incubated for 15 minutes and subsequently placed back into the gold container of the apparatus. The reagent bottle was then filled with an equal volume of endostatin (diluted in CAPS buffer at a concentration of 0.15 to 0.3 μg/ml. In an alternative embodiment, endostatin may be chemically modified by the addition of a sulfur group using agents such as n-succinimidyl-S-acetylthioacetate, to aid in binding to the gold particle.

The peristaltic pump was activated to draw the colloidal gold bound TNF and endostatin solutions into the T-connector. Upon complete interactions of the solutions the mixture was incubated in the collection bottle for an additional 15 minutes. The presence of additional binding sites for the PEG-Thiol was confirmed by the ability of salt to precipitate the particle at this stage. After the 15 minute incubation, 5K PEG-Thiol was added to the cAu$_{(TNF)}$-END vector and concentrated by diafiltration as previously described.

An alternative method for binding the two proteins to the same particle of gold comprising using the same apparatus as FIG. 1 and adding the agents simultaneously to the gold. TNF and END were placed in the reagent chamber of the binding apparatus. The concentration of each protein was 0.25 μg/ml and as a result, 1 ml of solution contained 0.5 μg of total protein. After binding the dual agent composition to gold particles, this colloidal gold preparation also precipitated in the presence of salt, indicating that additional free binding sites were available to bind the PEG-thiol. After a 15 minute incubation, 5K PEG-Thiol was added to the cAu$_{(TNF)}$-END vector and subsequently processed as described above.

Figure 8:
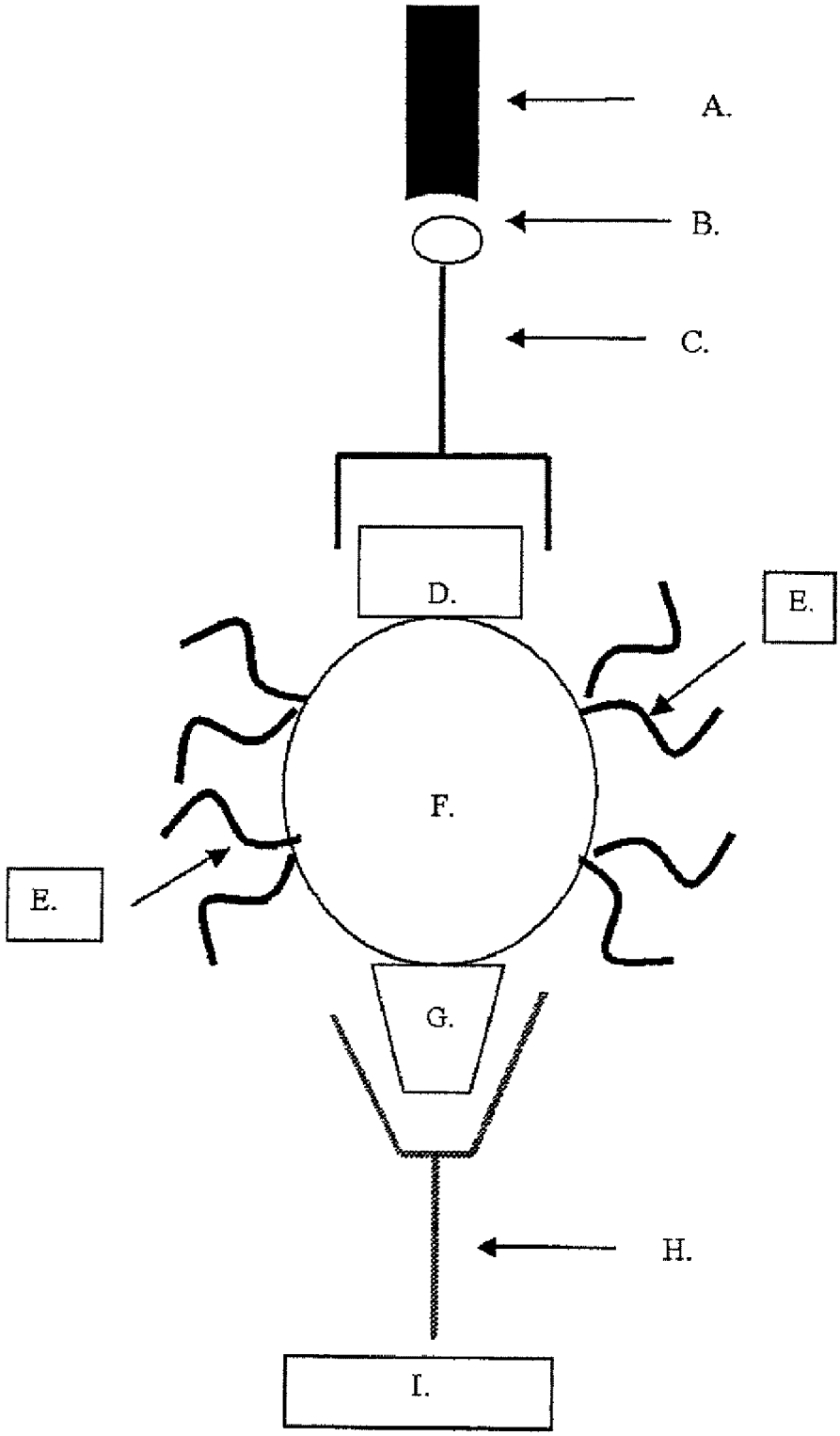
FIG. 8 is a schematic of an embodiment of a capture method for detecting a vector.

After diafiltration, the retentate was measured for TNF and END concentrations in their respective EIA. To confirm the presence of END and TNF on the same particle of colloidal gold, a cross-antibody capture and detection assay was designed and used. A schematic representation of this EIA is shown in FIG. 8. In FIG. 8, A=a labeled binding partner, such as streptavidin alkaline phosphatase; B=the binding partner, such as biotin; C=detection antibody, such as biotinylated anti-END antibody; D=an agent, such as an END molecule; F=a colloidal gold particle; E=derivatized PEG; and G=a different agent or targeting molecule, such as a TNF molecule; H=a capture antibody; such as anti-TNF antibody; and L=a support, such as a bead or a microtiter plate.

Figure 9:
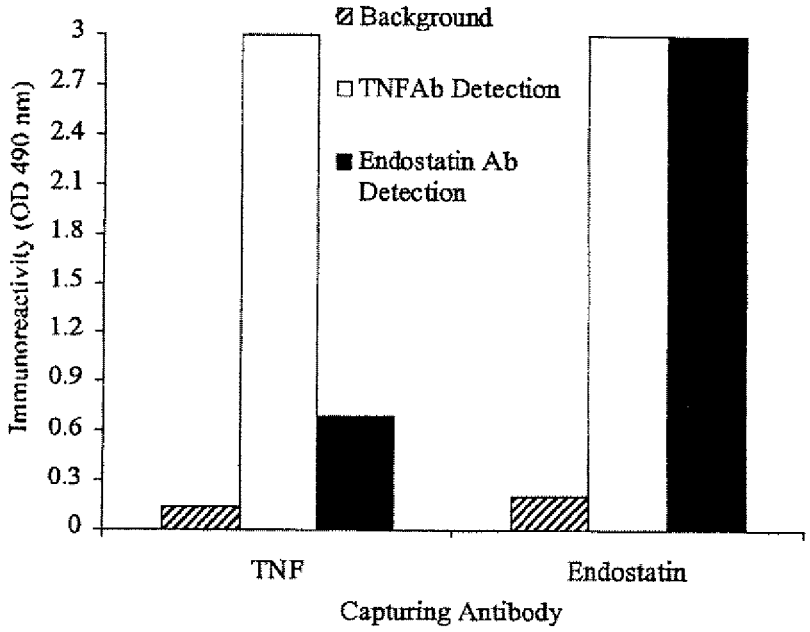
FIG. 9 is a graph showing TNF- and END-captured vectors exhibiting the presence of the second agent.

Samples of the PT-cAu$_{(TNF)}$-END vector were added to EIA plates coated with either the TNF or END capturing antibodies. The samples were incubated with the capturing antibody for 3 hours. After incubation the plates were washed and blotted dry. To bind any END present on a TNF captured sample, a biotinylated rabbit anti-endostatin polyclonal antibody was added to the wells. After a 30-minute incubation, the plates were washed and the presence of the biotinylated antibody was detected with streptavidin conjugated alkaline phosphatase. The generation of a positive color signal by the endostatin detection system indicated that the detection antibody bound to the chimeric vector previously captured by the TNF monoclonal antibody. See FIG. 9. By reversing the capturing and detection antibodies and using appropriate secondary detection systems, an assay was used to detect the presence of TNF on an END-captured particle. See FIG. 9. FIG. 9 is a graph showing TNF- and END-captured vectors exhibiting the presence of the second agent.

The data from these studies are presented in Table VI. As can be seen in Table VI, the retentate of the vector samples had 17 μg/ml of TNF and 22 μg/ml of END. These same samples also generated positive signals in the cross-antibody assays suggesting that both TNF and endostatin were on the same particle of colloidal gold (FIG. 9).

TABLE VI

The TNF and Endostatin concentrations present in retentates of the PT-cAu$_{(TNF)}$-END vector.

| Sample | Analyte Tested | Concentration |
|---|---|---|
| PT-cAu$_{(TNF)}$-END | TNF | 17 μg/ml |
| | END | 22 μg/ml |

Figure 10:
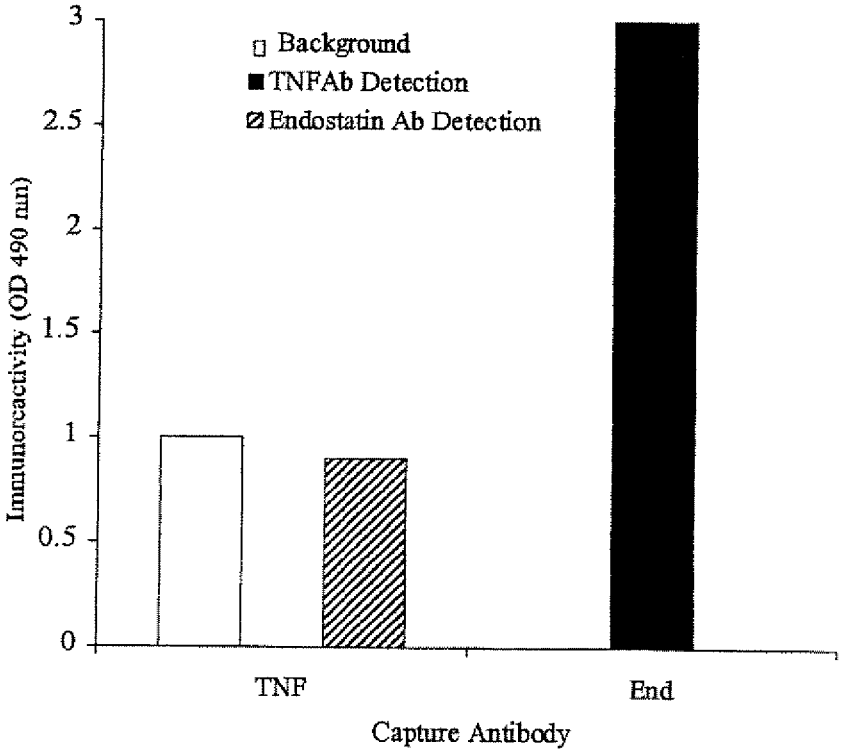
FIG. 10 is a graph showing TNF- and END-captured vectors exhibiting the presence of the second agent.

In FIG. 10 are the data showing the detection of endostatin and TNF from the PT-cAu$_{(TNF)}$-END vector in resected MC-38 tumors following intravenous injection. These data show that the PT-cAu(TNF)-END vector reached the tumor without degradation, since both molecules were detected in the tumor tissue.

It must be noted that, as used in this specification and the claims, the singular forms "a," "an," and "the" include plural referents unless the context clearly dictates otherwise. Thus, for example, reference to a vector composition containing "an agent" means molar quantities of such an agent.

It is to be understood that this invention is not limited to the particular combinations, methods, and materials disclosed herein as such combinations, methods, and materials may vary somewhat. It is also to be understood that the terminology employed herein is used for the purpose of describing particular embodiments only and is not intended to be limiting.

What is claimed is:

1. A composition [comprising] *for treating a solid tumor consisting essentially of* a pegylated colloidal gold particle *and an anti-cancer therapeutic agent*, wherein a polyethylene glycol derivative is covalently bound to the colloidal gold particle.

[2. The composition of claim 1, further comprising an anticancer therapeutic agent.]

3. The composition of claim [2] *1*, wherein the anti-cancer therapeutic agent comprises endostatin, angiostatin, thalidomide, taxol, melphalan, paclitaxel, taxanes, vinblastin, vincristine, doxorubicin, tumor necrosis factor, acyclovir, cisplatin or tacrine.

[4. The composition of claim 1, further comprising a targeting molecule.]

5. The composition of claim 1, [further comprising] *wherein the anti-cancer therapeutic agent is bound to the colloidal gold particle by* an integrating molecule.

6. The composition of claim 1, wherein the polyethylene glycol derivative is a polyethylene glycol-thiol derivative.

[7. The composition of claim 1, further comprising an immunostimulating molecule.]

[8. The composition of claim 7, wherein the immunostimulating molecule is selected from the group consisting of Interleukin-1, Interleukin-2, Interleukin-3, Interleukin-4, Interleukin-5, Interleukin-6, Interleukin-7, Interleukin-8, Interleukin-10, Interleukin-11, Interleukin-12, Interleukin-13, lipid A, phospholipase A2, endotoxins, staphylococcal enterotoxin B, Type I Interferon, Type II Interferon, Tumor Necrosis Factor alpha, Transforming Growth Factor beta, Lymphotoxin, Migration Inhibition Factor, Granulocyte-Macrophage Colony-Stimulating Factor, Monocyte-Macrophage Colony-Stimulating Factor, Granulocyte Colony-Stimulating Factor, Angiogenin, transforming growth factor alpha, fibroblast growth factor, cancer cell specific antigens, MART, MAGE, RAGE, B7 family of molecules and receptors, CD40 ligand/receptor, basic fibroblast growth factor, and vascular endothelial growth factor.]

*9. The composition of claim 1, wherein the anti-cancer therapeutic agent is tumor necrosis factor alpha.*

* * * * *